(12) United States Patent
Shuman et al.

(10) Patent No.: US 11,284,937 B2
(45) Date of Patent: Mar. 29, 2022

(54) FLEXIBLE RF ABLATION NEEDLE

(71) Applicant: Spiration, Inc., Redmond, WA (US)

(72) Inventors: Brandon J. Shuman, Kirkland, WA (US); Hugo Xavier Gonzalez, Woodinville, WA (US); Sean D. Alm, Snohomish, WA (US); Peter Hoffman, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 403 days.

(21) Appl. No.: 16/673,616

(22) Filed: Nov. 4, 2019

(65) Prior Publication Data

US 2020/0060755 A1    Feb. 27, 2020

Related U.S. Application Data

(62) Division of application No. 14/198,834, filed on Mar. 6, 2014, now Pat. No. 10,499,980.

(60) Provisional application No. 61/785,888, filed on Mar. 14, 2013.

(51) Int. Cl.
*A61B 18/14*  (2006.01)
*A61B 18/00*  (2006.01)
*A61B 90/00*  (2016.01)

(52) U.S. Cl.
CPC ...... *A61B 18/1477* (2013.01); *A61B 18/1492* (2013.01); *A61B 2018/00541* (2013.01); *A61B 2018/00982* (2013.01); *A61B 2018/1425* (2013.01); *A61B 2018/1435* (2013.01); *A61B 2018/1467* (2013.01); *A61B 2018/1475* (2013.01); *A61B 2090/3784* (2016.02)

(58) Field of Classification Search
CPC ............ A61B 18/1492; A61B 18/1477; A61B 2018/00196; A61B 2018/00273; A61B 2018/00279; A61B 2018/1427; A61B 2018/1432; A61B 2018/1472
See application file for complete search history.

(56) References Cited

U.S. PATENT DOCUMENTS

| | | | | |
|---|---|---|---|---|
| 5,972,026 A | * | 10/1999 | Laufer | A61B 18/00 606/41 |
| 7,628,789 B2 | * | 12/2009 | Soltesz | A61M 16/0463 606/41 |
| 8,007,496 B2 | * | 8/2011 | Rioux | A61B 18/1492 606/41 |
| 2007/0179494 A1 | * | 8/2007 | Faure | A61B 18/1477 606/41 |

* cited by examiner

*Primary Examiner* — Ronald Hupczey, Jr.
(74) *Attorney, Agent, or Firm* — Clements Bernard Baratta Walker; Michael S. Smith

(57) ABSTRACT

Embodiments disclosed herein are directed to devices, methods, and systems for the treatment of tissue using energy delivery. Specifically, certain embodiments may be used for the treatment of lung tissue, such as lung nodules, using RF ablation, via a catheter provided with a first electrode attached to a distal end of the catheter, wherein the first electrode is hollow, wherein the first electrode comprises a piercing tip configured to pierce through an airway wall and a second electrode received in a movable manner within the first electrode, wherein the second electrode is extendable from the first electrode to form a first extended configuration.

5 Claims, 17 Drawing Sheets

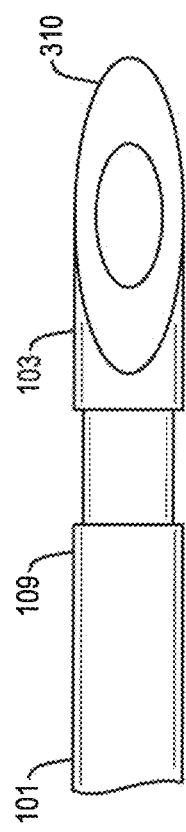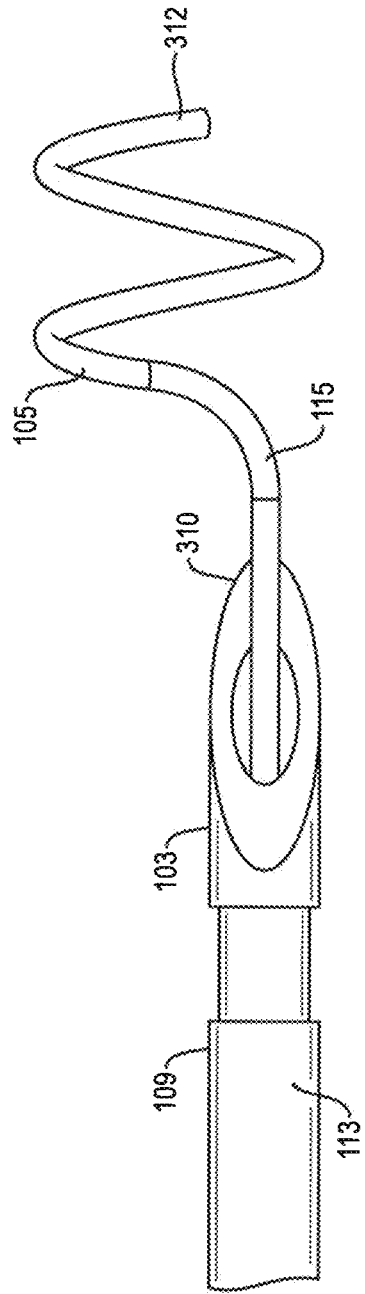
FIG. 3A
FIG. 3B

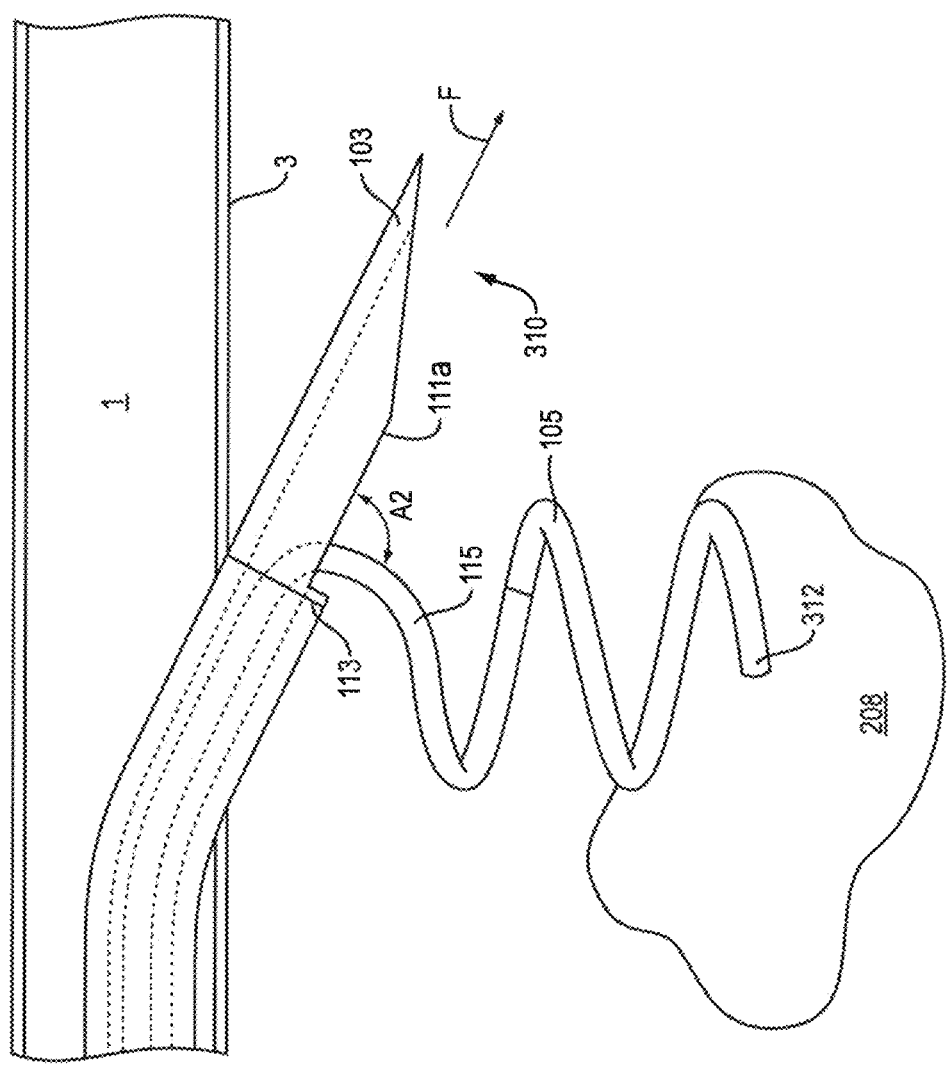

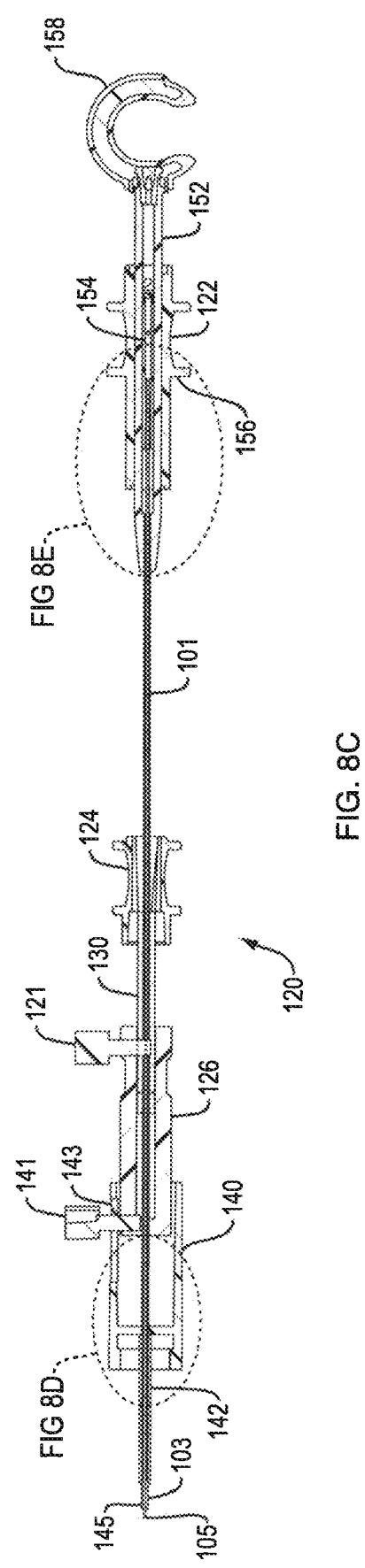

FLEXIBLE RF ABLATION NEEDLE

CROSS REFERENCE TO RELATED APPLICATIONS

This application is a Divisional Application of U.S. patent application Ser. No. 14/198,834 filed Mar. 6, 2014, and issued as U.S. Pat. No. 10,499,980 which claims priority to and the benefit of U.S. provisional patent application Ser. No. 61/785,888 filed on Mar. 14, 2013 entitled "Flexible RF Ablation Needle," the entire disclosure of which is hereby incorporated by reference as if set forth in its entirety for all purposes.

BACKGROUND

Technical Field

The present invention generally relates to the treatment of tissue via energy delivery. More particularly, certain embodiments of the present invention relate to thermal ablation of lung tissue with energy delivered via a piercing needle.

Description of the Related Art

Lung cancer has a high incidence of morbidity and mortality in patients. Early stages of lung cancer can take the form of pulmonary nodules (in particular those under between 0.5 mm and 30 mm in size) and may require careful evaluation by a medical professional, especially in patients that have risk factors such as tobacco use or a family history of cancer.

Lung nodules, lesions, tumors, and other cancerous or pre-cancerous regions of tissue in the lung, may be difficult to treat with invasive surgical techniques, with attendant complications such as excessive bleeding, infection risk, air leaks, pneumothorax, and other such issues. In particular, regions deep in the lung may be difficult to access using conventional methods, further increasing the difficulty of treatment.

Electrical ablation, in particular radiofrequency electrical ablation, has been used in the treatment of tumors and other masses present in solid tissues such as the liver. Use of such techniques in the lungs, however, entails some attendant complications and difficulties. First, the use of conventional electrical ablation probes requires piercing into the thoracic cavity and into the lung, with a consequent high likelihood of pneumothorax, excessive bleeding and other complications. Moreover, these transthoracic ablation probes are rigid and may not be able to reach certain areas of the pulmonary anatomy.

While there have been some attempts to pursue radiofrequency electrical ablation via bronchoscopes inserted into airways, these attempts are limited by the confines of the airway passage and the reach of the bronchoscope—which cannot enter into very small peripheral lung passages—and accordingly may not be able to position the probes and/or deliver sufficient energy to treat tissue such as lung nodules adequately. Damage to the airway itself may result from the treatment process. Additionally, it will be noted that visualization and localization of the tissue region to be treated may present challenges, especially for tissue regions deep in the lung.

SUMMARY

It is therefore a goal of the embodiments described herein to provide new devices, systems, and methods for the treatment of tissue, in particular lung tissue and lung nodules.

In a first embodiment, a device for the delivery of energy to a region of lung tissue, the device comprises:
 a catheter configured to be inserted into an airway;
 a first electrode attached to the distal end of the catheter, wherein the first electrode is hollow, wherein the first electrode comprises a piercing tip configured to pierce through an airway wall;
 a second electrode received in a movable manner within the first electrode, wherein the second electrode is extendable from a distal end of the first electrode to form a first extended configuration;
 a handle attached at a proximal end of the catheter, wherein the handle comprises a second activation toggle configured to extend the second electrode from the first electrode; and
 a first electrical lead in electric communication with the first electrode, and a second electrical lead in electric communication with the second electrode, wherein the first and second electrical leads are connectable to a source of electric power.

In some embodiments, the catheter is dimensioned to be insertable into a bronchoscope. In some embodiments, the bronchoscope comprises a side-facing ultrasound probe. Preferably, the first electrode may be flexible. In some embodiments, the first electrode may be bendable to an angle of at least 10° relative to a first longitudinal axis defined relative to the longitudinal axis of the axial length of the airway. In a further embodiment, the second electrode, when in a first extended configuration, forms a coil. In some embodiments, the coil is configured to corkscrew into at least part of the region of lung tissue. Further embodiments may comprise the second electrode being constructed at least in part from a shape-memory material having a martensite configuration at a first lower temperature, and an austenite configuration at a second temperature above body temperature, and wherein the second electrode is configured to adopt a first straight configuration while in the mallet/site configuration, and a bend or coil while in the austenite configuration. The second electrode may adopt the austenite configuration when in the first extended configuration.

In some embodiments, the handle further comprises a first activation toggle configured to extend the first electrode. In some embodiments, the second activation toggle is connected to the first activation toggle, and wherein the first and second electrodes are flexible and connect the second activation toggle to the first activation toggle. In a further embodiment, the second activation toggle comprises a movable grip configured to move in a longitudinal axial direction with respect to a static grip. The second activation toggle may be configured to deploy the second electrode when the movable grip is moved in a longitudinal axial direction with respect to the static grip.

In some embodiments, the handle further comprises a bronchoscope attachment configured to attach to the working channel of a bronchoscope. Preferably, the bronchoscope attachment may comprise a bronchoscope guide configured to be inserted at least partially into the working channel of the bronchoscope. In some embodiments, the catheter may further comprise a guide sheath disposed over at least a portion of the catheter shaft. Preferably, the source of electric power comprises a radiofrequency generator. The first and second electrodes may comprise a bipolar radiofrequency ablation electrode.

Some embodiments further comprise a fluid source connected to the catheter and in fluid communication with at least one of the first or second electrodes. In some embodiments, the fluid source is configured to flow out of the first electrode. The catheter may comprise a fluid injection port configured to be attached to the fluid source. The fluid source may comprise a saline solution. The fluid source may comprise a visualization agent. The fluid source may comprise a medicant. In some embodiments, the fluid source circulates within one or both of the first and second electrodes without flowing out of the first and second electrodes.

In some embodiments, the device further comprises an impedance detector attached to one or more of the first and second electrodes, the impedance detector configured to detect the impedance of the surrounding tissue. The device may further comprise a temperature sensor configured to detect the temperature of the surrounding tissue. The temperature sensor may be attached or integrated to one or more of the first and second electrodes. The temperature sensor may be separate from the first and second electrodes. Some embodiments further comprise a feedback mechanism configured to change the amount of power applied to the tissue in response to one or more monitored attributes. The one or more monitored attributes may be selected from the group consisting of tissue temperature, tissue impedance, amount of fluid delivered, energy, and time. In some embodiments, the feedback mechanism is configured to stop the application of power applied to the tissue in response to a level of the one or more monitored attributes exceeding a predetermined limit.

In a second embodiment, a method of delivering energy to a region of lung tissue to be treated, the method comprises:
  inserting a catheter into a patient's airway, wherein the distal end of the catheter comprises a first electrode and a second electrode received in a sliding manner within the first electrode and configured to be extendable therefrom;
  navigating the catheter to an airway proximate the region of lung tissue to be treated;
  piercing the airway with the first electrode so as to position the first electrode into or near the region of lung tissue to be treated;
  extending the second electrode into the region of lung tissue to be treated;
  activating a power source configured to deliver a therapeutic amount of energy to the region of lung tissue to be treated, wherein the power source is connected via a first electrical lead connected to the first electrode and a second electrical lead connected to the second electrode; and
  delivering energy to the region of lung tissue to be treated.

In some embodiments, the energy delivered to the region of lung tissue comprises radiofrequency ablation. Some embodiments further comprise bending at least the first electrode at an angle relative to and non-parallel to a first longitudinal axis defined relative to the axial length of the catheter. Some embodiments further comprise inserting the catheter into a bronchoscope, the bronchoscope being inserted into the patient airway. In some embodiments, the bronchoscope comprises an ultrasound sensor, and wherein the ultrasound sensor is used to navigate the catheter. In some embodiments, the ultrasound sensor faces at a direction perpendicular the first longitudinal axis. The catheter may be navigated to the region of lung tissue to be treated by one or more methods selected from the group consisting of fluoroscopy and real-time computerized tomography. Some embodiments further comprise monitoring at least one monitored attribute associated with the delivery of energy to the region of lung tissue to be treated. In some embodiments, the at least one monitored attribute is selected from the group consisting of tissue temperature, tissue impedance, and time. Some embodiments further comprise changing the amount of power delivered by the power source in response to a feedback mechanism responsive to at least one monitored attribute. Some embodiments further comprise stopping the application of power applied to the tissue in response to a level of the one or more monitored attribute exceeding a predetermined limit.

In another embodiment, a system for the delivery of energy to a region of lung tissue, the system comprises: an energy delivery device comprising: a catheter configured to be inserted into an airway, the catheter comprising a first electrode and a second electrode; a handle attached at a proximal end of the catheter, the handle comprising a second activation toggle configured to extend the second electrode from the first electrode; wherein the second electrode is received in a movable manner within the first electrode, and wherein the second electrode is extendable from a distal end of the first electrode to form a first extended configuration; a power source connected to the first electrode and second electrode via first and second electrical leads, the power source configured to deliver RF energy; and a conduit insertable into an airway and selected from the group consisting of a bronchoscope and guide sheath, the catheter being insertable and movable therein.

In some embodiments, the system further comprises a fluid source connected to the device and configured to deliver fluid out of a distal end of the catheter. Some embodiments may comprise one or more additional sensors configured to monitor one or more monitored attributes of the system, wherein the one or more monitored attributes are selected from the group consisting of: temperature, electrical parameters, and fluid flow rate. Some embodiments further comprise a feedback system responsive to at least one of the monitored attributes, wherein the feedback system is configured to change or stop one or more treatment attributes.

BRIEF DESCRIPTION OF THE DRAWINGS

These and other features, aspects and advantages of the present disclosure will now be described with reference to several drawings, which drawings are intended to be illustrative and not limiting.

FIGS. 3A and 3B illustrate two electrodes of the catheter of FIG. 1 in undeployed and deployed position, respectively.

FIG. 3G illustrates a distal end of a catheter having two electrodes deployed through the wall of an airway or other body lumen.

FIGS. 8A-8D illustrate another embodiment of a handle portion of a catheter that is arranged and configured in accordance with certain features, aspects and advantages of an embodiment of the present disclosure.

DETAILED DESCRIPTION

Embodiments of an apparatus, system, and method for identification and treatment of regions of the lung, and in particular, pulmonary nodules and lesions, will be described with reference to the accompanying figures of one or more embodiments. The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

The terms "lung region," "lung area," "tissue," "lesion" and "nodule" as used herein are broad interchangeable terms and, unless otherwise indicated or apparent from the context of use, the terms can include within their meaning, and without limitation, other organs or regions of tissue in a human or animal body, including diseased, cancerous, and/or pre-cancerous tissue, as well as tissue showing lesions, or generally any tissue region for which treatment is desired. Although some embodiments described herein refer to identifying and treating an area within a lung, this disclosure is not so limited, and the embodiments described herein may be used in other vessels, passages, body cavities, and organs in humans and animals. For example, the methods and apparatuses described herein can be used to treat abdominal organs, lymphatic system, prostate, urinary tract (including bladder), genital organs, breasts and/or other areas/systems of the body.

Figure 1:
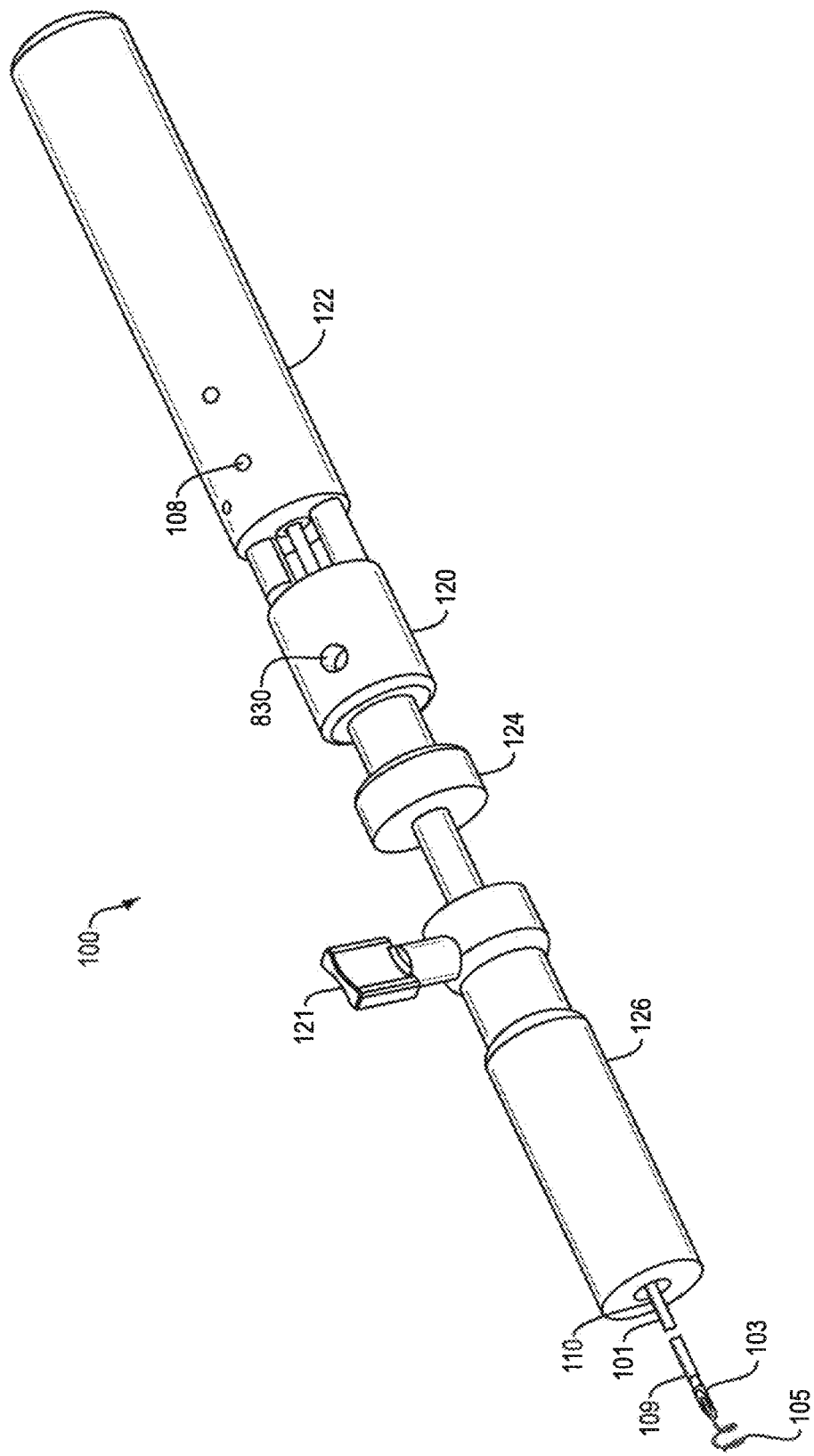
FIG. 1 illustrates an embodiment of a catheter that is arranged and configured in accordance with certain features, aspects and advantages of an embodiment of the present disclosure.

FIG. 1 illustrates an embodiment of a catheter system 100 that is arranged and configured in accordance with certain features, aspects and advantages of the present invention.

The illustrated catheter system 100 comprises a catheter shaft 101 connected to a handle 120. The handle 120 preferably is configured to be gripped by one hand of a user (e.g., a doctor, nurse, or other health professional).

The handle 120 may comprise a thumb pad 121. The thumb pad 121 may provide additional support when the handle 120 is being held. One or more surfaces of the handle 120 also may be designed to be grippable. In some configurations, at least a portion of the grippable portions of the handle 120 may comprise knurling, rubberized surfaces or the like to improve the ability to maintain a grip on the handle 120, for example but without limitations.

In some configurations, the thumb pad 121 may be connected to, or otherwise act as, a clamp. For example, the clamp can be used to maintain a position of the catheter shaft 101 relative to the handle 120. For example, the thumb pad 121 may be configured with a twisting screw engagement that allows a portion of the handle 120 to clamp onto the catheter shaft 101, which can extend at least partially through the handle 120. Other configurations also can be used to secure the catheter shaft 101 in position relative to the handle 120.

The catheter shaft 101 can be connected at its proximal end 110 to the handle 120. As will be explained in greater detail below, the catheter shaft 101 may have a first electrode 103 at a distal end 109 of the catheter shaft 101. In some configurations, the catheter shaft 101 can comprise a second electrode 105. The second electrode 105 can be movable relative to the first electrode 103. In some configurations, the second electrode 105 can be received in a movable manner within the first electrode 103. In some configurations, the second electrode 105 can be extendible from the first electrode 103.

As will be discussed below, a first electrode 103 and a second electrode 105 can be electrically connected to a first electrical lead 107 and a second electrical lead 108, respectively. The electrical lead 107 can be on an opposite side of a fluid port 830 relative to a first electrical toggle 124. The first electrical lead 107 is visible in FIG. 7.

Figure 2:
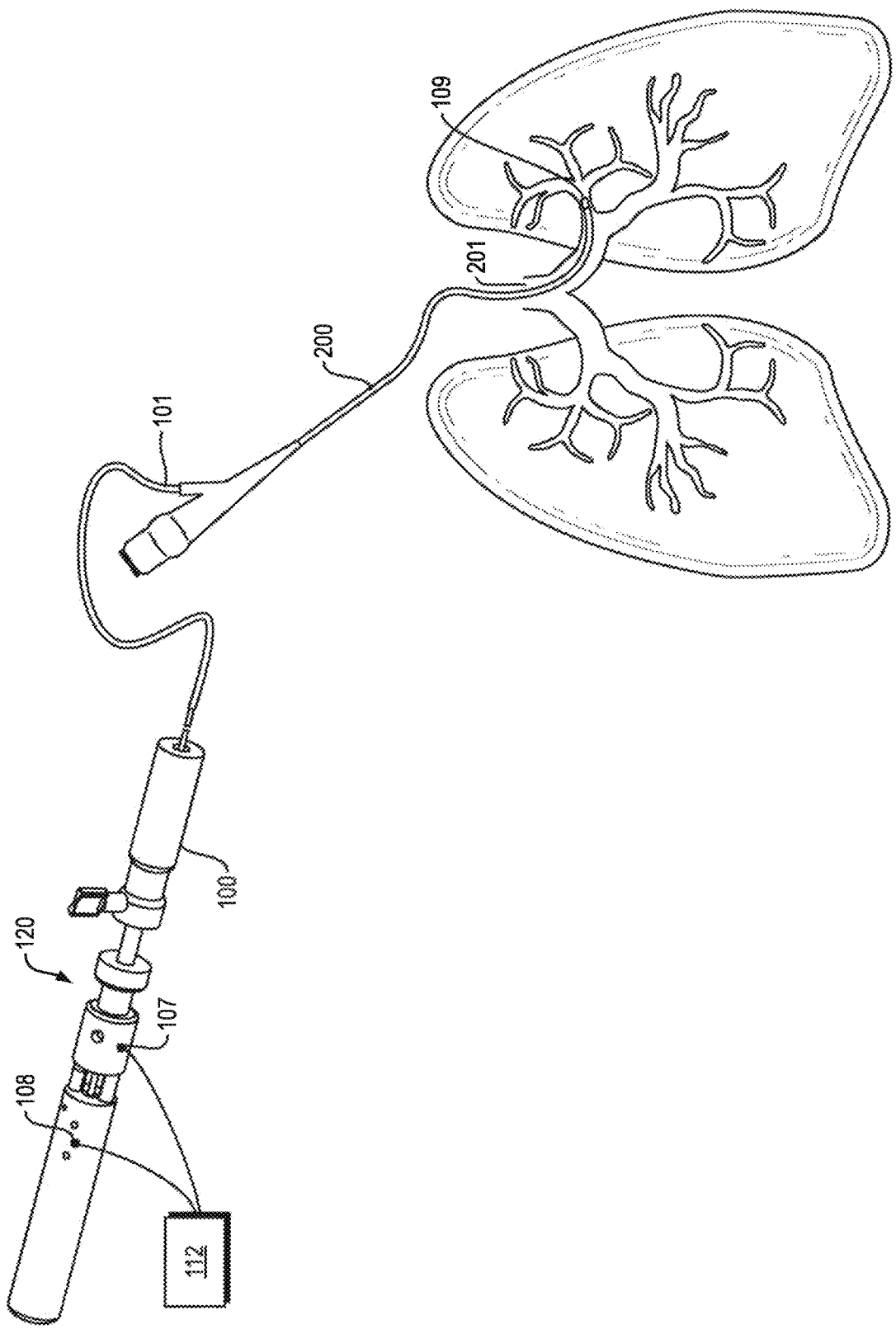
FIG. 2 illustrates the catheter of FIG. 1 being inserted through a bronchoscope and into an airway.

As shown in FIG. 2, a power source 112 may be connected to the first and second electrical leads 107, 108, for example via wires and the like. As such, the power source 112 can deliver power to the first electrode 103 and/or the second electrode 105 through the first and second electrical leads 107, 108. Thus, the power source 112 can be configured to deliver energy to a region of tissue via the catheter system 100, which includes one or more of the first and second electrodes 103, 105.

In some configurations, the power source 112 comprises a source of electric or electromagnetic power. Other sources of energy, alone or in combination, can be used and energy can be delivered to the tissue via the power source 112 and/or the catheter system 100. Such power sources can include direct current treatment, cryo treatment (including cryoablation), microwave, laser, and/or photodynamic treatment, for example but without limitation.

In some configurations, the power source 112 may be configured to deliver electric power at varied frequencies. In some configurations, the power source 112 can be configured to deliver radiofrequency ("RF") energy in a range of between about 3 KHz and about 300 GHz. In some configurations, the power range is between about 100 KHz and about 500 KHz. In some configurations, the power range is between about 300 KHz and about 400 KHz.

In some configurations, the power source 112 can deliver power in a range of between about 5 watts and about 40 watts. For some therapeutic treatments, the range can be between about 7 watts and about 25 watts. In some configurations, the range can be between about 8 watts and about 13 watts.

In some configurations, the power level can be set by the user or operator, and the resulting voltage and current will vary in accordance with that setting. In some configurations, the voltage and the current can vary between the ranges of about 20 VAC and about 60 VAC and between about 0.1 ampere and about 1 amperes.

In some configurations, the energy delivered to a 1 cm diameter volume treatment site is between about 8 KJ and about 13 KJ, depending upon the tissue type. As explained below in greater detail, the energy delivered to the tissue affects the tissue ablation area.

In some configurations, the system 100 acts to heat or ablate tissue via RF energy, although such treatment is also possible by using other energy delivery techniques. In particular, tissue such as tumors (especially lung nodules) or other tissue masses may be treated with energy so as to heat the cells therein to ablate, kill, burn, heat, or denature the cells. The tissue may not necessarily need to be heated so as to kill the component cells, but may be heated enough to modify the cells so as to become non-malignant or otherwise benign. As described above, in some configurations, this may also be achieved by cooling the respective tissue area, for example via cryoablation.

In some configurations, energy such as RF energy may be delivered via a single electrode, e.g., the electrode 103. In such configurations, the electrical field can emanate away from the electrode as a single point source. In other configurations, energy may be delivered via a bipolar electrode. In such configurations, and as described further herein, the electrical field may emanate between two respective poles of the electrodes (e.g., electrodes 103, 105). Such configurations may be advantageous in facilitating adjustment of the treatment zone in the tissue region to be treated. Other configurations also are possible, including the use of multipolar electrodes or multiple separate electrodes.

With reference now to FIG. 2, the catheter system 100 may be used for treatment of tissue, for example pulmonary tissue. In some embodiments, the catheter system 100 is configured to be used in thoracoscopic, laparoscopic, transcutaneous, and/or percutaneous procedures. In some such embodiments, the catheter system 100 can be navigated to the nodule or other site of interest within the body via fluoroscopy, tomography or other external visualization techniques. In some configurations, the catheter shaft 101 can be insertable into a bronchoscope 200. Various types of bronchoscopes may be used, including but not limited to the BF-P180 bronchoscope manufactured by Olympus. Bronchoscopes using ultrasound probes or other visualization devices also can be used, including the EBUS® scope manufactured by Olympus (described in greater detail in FIG. 4 below). While the handle 120 is illustrated in FIG. 2 at a distance from the bronchoscope 200 (and its working channel) for clarity, the handle 120 generally will be placed close to, or in contact with, the working channel of the bronchoscope 200.

In some configurations, the catheter shaft 101 can be inserted into an airway 201 so that the distal end 109 of the catheter shaft 101 reaches or is placed proximate a region of tissue to be treated. For example, the catheter 101 can be inserted into the bronchoscope 200, which has been inserted into the airway 201. Other configurations also are possible. For example, when used relative to other body tissues and/or in other body lumens (e.g., during intestinal or colonoscopic treatments), the system 100 can be loaded into other types of endoscopes. As will be described in greater detail below, the catheter system 100 can comprise a piercing component that is able to pierce through an airway wall or lumen after the catheter shaft 101 is placed proximate a region of tissue to be treated, such as a lung nodule, for example but without limitation. In other words, after the catheter shaft 101 passes along one or more airway of the lung, the piercing component of the catheter system 100 can be used to pierce an airway wall or lumen to gain access to tissue, nodules or the like outside of the airway. In some configurations, the catheter system 100 can be passed through an airway and then extend into tissue outside of the airway while remaining within the pleurae. In some configurations, the catheter system 100 enables piercing through the airway without contacting the chest wall. In some configurations, the catheter system 100 may be used without an endoscope, and may be used, for example but without limitation, in transthoracic or laparoscopic surgical interventions. In some configurations, it is contemplated that features may be added to the first electrode, the second electrode, or both to enhance visualization with x-ray fluoroscopy or ultrasound, for example. In some configurations, the surface area of the second electrode may be greater than the surface area of the first electrode. In some embodiments, a saline passage is provided along the internal surface of the first electrode. The surface area of the first electrode may be smaller than the surface area of the second electrode with the use of a fluid source delivering saline or other fluids to the treatment area.

FIGS. 3A-3B illustrate the distal end 109 of the illustrated catheter shaft 101, which has been arranged and configured in accordance with certain features, aspects and advantages of the present invention. As illustrated, the distal end 109 may comprise one or more of the first and second electrodes 103, 105. In some configurations, more than two electrodes can be positioned at or near the distal end 109. In some configurations, less than two electrodes can be positioned at or near the distal end 109. For example, one electrode can be positioned at or near the distal end 109 and a patient pad can serve as the second electrode. Some configurations may provide for the first electrode 103 being provided separately from the second electrode 105, or for three, four, or more electrodes being used to treat a region of tissue. For example, multiple catheters may be used to place the multiple electrodes into contact with the tissue region to be treated.

In some configurations, the extreme distal portion of the distal end 109 can provided with a piercing tip 310. The piercing tip 310 may be a separate component from the electrode 103. In some configurations, the piercing tip 310 can be a separate component from the electrode 103 but the separate piercing tip 310 can be attached to the electrode 103. In some configurations, the piercing tip 310 can be adhered to the electrode 103. In some configurations, the piercing tip 310 can be formed integrally with the electrode 103 such that the piercing tip 310 and the electrode 103 are monolithic and unitary in construction. The piercing tip 310 can be formed, for example, by beveling or otherwise sharpening the distal end of the electrode 103.

The piercing tip 310 can be configured with a sharp edge 311 or end that may pierce, perforate, or penetrate into tissue, for example an airway wall. In some configurations, the first electrode 103 can be positioned at the distal end 109, and even more preferably can be attached to, integrated to, or connected to the piercing tip 310. In other words, a portion of the first electrode 103 can be configured to comprising the piercing tip 310 such that the first electrode 103 can pierce the airway wall.

The second electrode 105 may be configured to be received in a movable manner within or adjacent to the first electrode 103. In some configurations, the second electrode 105 can be extendible relative to the first electrode and/or the first electrode 103 can be extendible relative to the second electrode 105. In some configurations, the handle 120 may be used to move the second electrode 105 relative to the first electrode 103. Such a configuration will be described below with reference to FIGS. 6A-6C. In such a configuration, the second electrode 105 may be movable along a longitudinal axis of the catheter shaft 101 in, for example, a sliding manner.

Where the second electrode 105 is disposed within the first electrode 103, only one electrode may need to be sufficiently strong to pierce through an airway wall (e.g., with the piercing tip 310), rather than needing two separate electrodes possessing sufficient strength or rigidity or being provided with piercing tips arranged to puncture the airway wall. On the other hand, in some configurations, the second electrode 105 may be provided with, or attached to, a piercing end 312. The piercing end 312 can be used to penetrate into tissue being treated (e.g., a lung nodule). In some configurations, the piercing end 312 may be sheathed by the first electrode 103. In some configurations, the piercing end 312 may be exposed when the second electrode 105 is extended from the first electrode.

In some embodiments, the piercing end 312 may be flexible, but relatively straight except for a slight curve at a distal tip thereof. When inserted into tissue, the piercing end 312 may curve or form a spiral or coil. In some configurations, the piercing end 312 can be formed or arranged to take a helical or spiral form. Such configurations may be preferable because they may induce an eddy current into the tissue being treated, in addition to the joule heating resulting from a resistance of the tissue being treated. In some configurations, the piercing end 312 is flexible, and adapts a helical, spiral, or coiled configuration once extended away from the first electrode 103. In some configurations, the piercing end 312 may comprise a superelastic material (e.g., Nitinol) and the piercing end can change shapes. Other materials may also be used, including conductive polymers and bundles of multiple wires (such as a cable), which may in some configurations provide for greater elasticity.

As explained above, in some configurations, the piercing end 312 can be manufactured at least in part from a shape-memory material, such as Nitinol. In some such configurations, the piercing end 312 may have an austenite configuration above body temperature that forms a coil or bend. The piercing end 312 may be loaded into the device 100 in the martensite configuration and in a straighter form, such that heating of the piercing end 312 (e.g., due to electric current passing through the piercing end 312 or by contact of the piercing end 312 with warmer body tissue) causes the piercing end 312 to convert to the austenite configuration and form a bend or coil. In some configurations, the piercing end 312 may be deployed into tissue while still straight, followed by subsequent heating to cause it to change shape. In some configurations, the piercing end 312 may be heated as it is inserted into the tissue (e.g., as it exits the electrode 103) so that it begins to bend or coil as it is deployed. It is contemplated that deployment of the second electrode into a bent or coiled configuration may result in the electrode assembly entering a tissue locking position such that the distal tip of the device is maintained in position with respect to the treatment area of interest. Such a locking position may be maintained during breathing or heat treatment. It is contemplated that the second electrode may go through multiple deployment from the first electrode without moving the first electrode. It is contemplated that the result produced from applying electrical energy to the device of the present invention may be an egg shaped ablation area instead of a sphere shaped ablation area.

In some configurations, the outer dimensions of the coiled or helical piercing end 312 may be small enough to fit within the piercing end 310 without bending. In some configurations, the piercing end 312 can be configured to embed or fixate itself into the surrounding tissue when extended. For example, in some configurations, the piercing end 312 may corkscrew or spiral into the surrounding tissue. Preferably, the piercing end 312 may be shaped as a coil with a pitch in a range of between about 0.1 mm to about 2 mm, and preferably about 1 mm. The major diameter of the coil may measure between about 2 mm and about 10 mm, and preferably between about 3 mm and about 4 mm. The coil may also comprise between about 0.5 total turns and about 5 total turns, and preferably between about 1.5 total turns and about 3 total turns. The wire diameter that may be used to manufacture the coil may measure between about 0.010 inches and about 0.020 inches, and preferably about 0.015 inches.

In some configurations, at least one of the first electrode 103 and the second electrode 105 includes an insulating layer 113, 115. In some configurations, for example, an insulating layer 113, 115 can be positioned between the first electrode 103 and the second electrode 105. In some configurations, the insulating layer can be formed on an inner surface of the first electrode 103 and/or on an outer surface of the second electrode 105 (see, e.g., insulating layer 115 on the outer surface of the second electrode 105). Such a placement of the insulating layer(s) can serve to reduce the likelihood of short circuiting between the electrodes while improving the use of bipolar or multipolar ablation configurations. In some configurations, the first electrode 103 comprises an insulating layer 113 that terminates proximal of the distal extremity of the first electrode 103. In some such configurations, the insulating, layer 113 can be partially removed or stripped to expose one or more conductive surfaces of the first electrode 103.

In some configurations, insulating materials may be lubricious. Lubricious insulating materials can improve the ability of the electrodes 103, 105 to move relative to each other. Any suitable insulating material may be used to overlay at least a portion of the one or more electrodes. In some configurations, the insulating material may comprise a polymeric material. For example, PTFE, fluorinated ethylene propylene, high density polyethylene, polyethylene, and/or other suitable insulating materials may be used. In some embodiments, the use of saline (e.g., saline conductive gel) can reduce friction between the electrodes 103, 105. In some embodiments, one or more surfaces of the electrodes 103, 105 can be coated with a ceramic powder.

When using bipolar or multipolar electrical ablation, in particular RF ablation, the first and second electrodes 103, 105 can be used to concentrate the energy being delivered to the surrounding tissue into a zone roughly bounded by these electrodes 103, 105. The degree of extension of the second electrode 105 into the tissue permits the user to modulate the amount and area of energy being directed into the surrounding tissue. In some configurations, the first and second electrodes 103, 105 can be configured to limit the range of relative extension. For example, the range of relative extension between the first and second electrodes 103, 105 can be predetermined based upon the size of the nodule or other area of interest to be treated. In some embodiments, the deployed distance between the first and second electrodes 103, 105 is configured to be approximately equal to the depth of the nodule or other area of interest into which the first and/or second electrodes 103, 105 are deployed. In some configuration, the extent to which the first and second electrodes 103, 105 can move relative to each other in the distal and/or proximal directions is approximately equal to the distance required to move the proximal end of the second electrode 105 from the stored position to the deployed position. In some embodiments, the extent to which the first and second electrodes 103, 105 can move relative to each other in the distal and/or proximal directions is greater than the deployed distance between the first and second electrodes 103, 105 due, for example, to the second electrode 105 being stored in a relative straight configuration within the catheter shaft 101 prior to deployment.

Figure 3C:
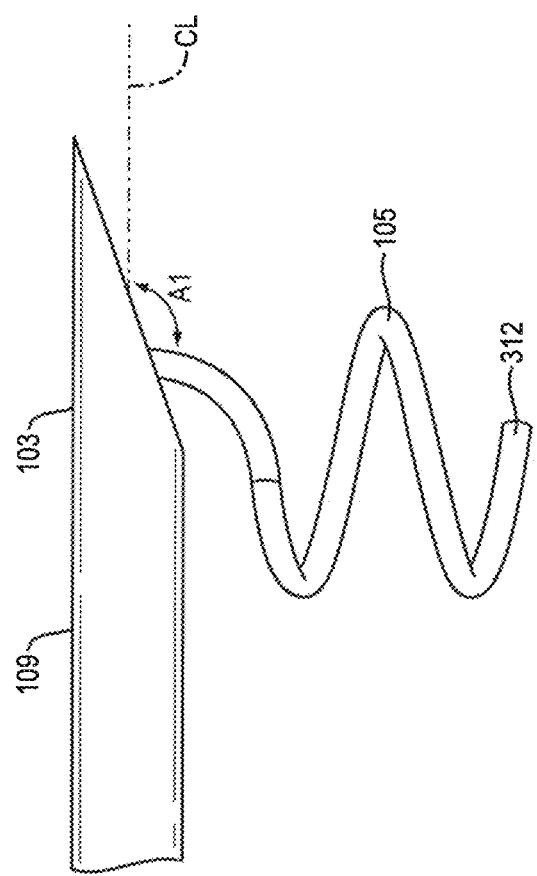
FIG. 3C illustrates a distal end of a catheter having two electrodes.
Figure 3D:
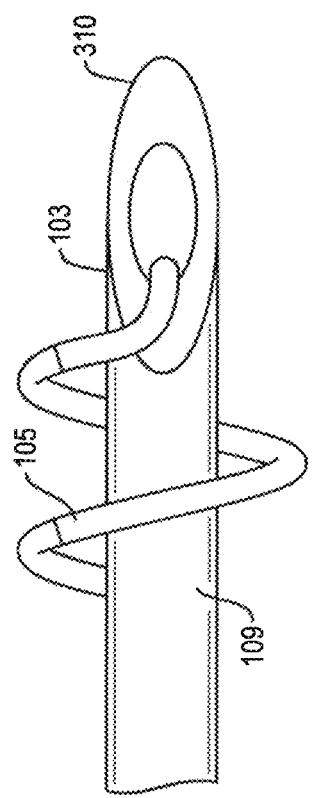
FIG. 3D illustrates a distal end of a catheter having two electrodes wherein one electrode wraps around the other.
Figure 3E:
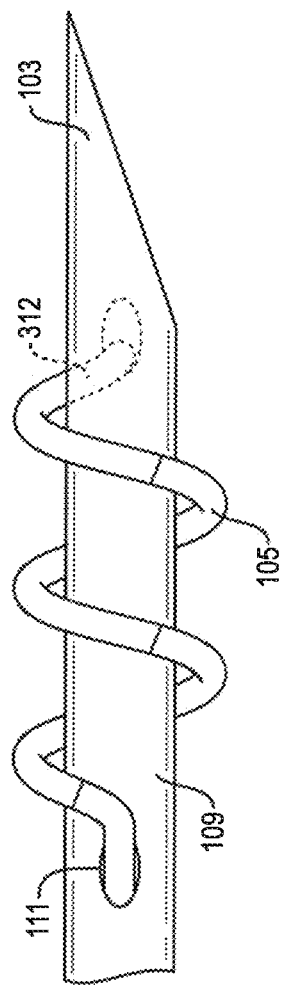
FIG. 3E illustrates a distal end of a catheter having two electrodes wherein one electrode spans an aperture in the catheter wall.

As illustrated in FIG. 3C, the second electrode 105 can be configured to extend from the first electrode at an angle A1 from the centerline CL of the first electrode 103. In some embodiments, the angle A1 at which the second electrode 105 is extended can be greater than or equal to about 0° and/or less than or equal to about 180°. In some embodiments, the angle A1 is approximately 90°. Many variations are possible. For example, FIG. 3D illustrates an embodiment wherein the angle A1 at which the second electrode 105 extends from the first electrode 103 is approximately equal to 180°. In some embodiments, the second electrode 105 is configured to wrap around the first electrode 103 and/or distal end 109 of the catheter shaft 101.

In some embodiments, the distal end 109 of the catheter shaft 101 can include one or more apertures 111. The second electrode 105 can be configured to extend through the aperture 111 when transitioned to the deployed position. In some such embodiments, the second electrode 105 can extend to a position proximal to, lateral to (e.g., the second electrode 105 can extend at an angle A1 from the centerline CL of the first electrode 103), and/or distal to the first electrode 103.

Figure 3F:
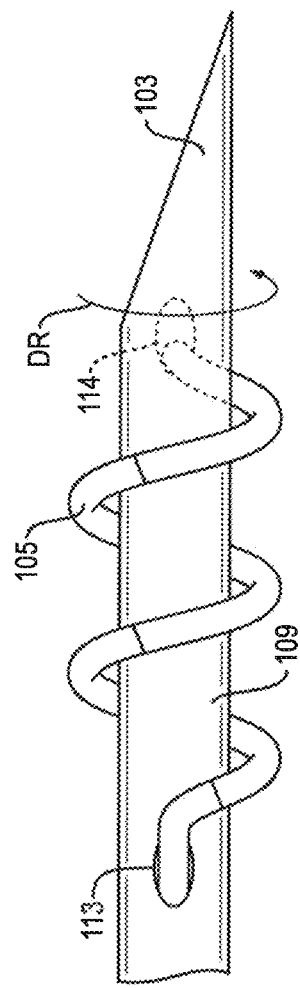
FIG. 3F illustrates a distal end of a catheter having two electrodes wherein one electrode wraps around the other and is attached to leads external to the catheter.

As illustrated in FIG. 3F, the second electrode 105 can be fixed to the exterior surface of the distal end 109 of the catheter shaft 101. For example, the second electrode 105 can be fixed to one or more conductive contact points 113, 114 configured to electrically connect the second electrode 105 to one or more of the first and second electrical leads 107, 108. In some embodiments, an externally-affixed second electrode 105 can be configured to function as an auger threading to permit the distal end 109 of the catheter shaft 101 to advance into tissue as the distal end 109 of the catheter shaft 101 is rotated (e.g., in rotation direction DR, as illustrated in FIG. 3F). The second electrode 105 can reduce or eliminate the likelihood of the electrodes 103, 105 detaching from the tissue into which they are inserted absent rotation of the distal end 109 of the catheter shaft 101 in a direction opposite the rotation direction DR.

In some embodiments, the piercing tip 310 of the first electrode 103 is used to pierce the wall 3 of an airway 1. The first electrode 103 and/or distal end 109 of the catheter shaft 101 can include a slot 111a. The slot 111a can extend through a side wall of the first electrode 103 from the distal end of the first electrode 103 to a point proximal to the distal end of the first electrode 103. The second electrode 105 can be configured to extend through the slot 111a at an angle A2 from the centerline of the first electrode 103 as the second electrode 105 deploys from the first electrode 103. The angle A2 can be greater than or equal to about 0° and/or less than or equal to about 180°. In some embodiments, the angle A2 is approximately 90°.

During deployment, the first electrode 103 can be advanced through an airway wall 3 tangentially to a nodule 208 or other site of interest outside of the airway 1. The second electrode 105 can be advanced at angle A2 from the first electrode 103 into the nodule 208. The piercing end 312 of the second electrode 105 can pierce the nodule 208. The piercing end 312 can, in some embodiments, include a barb or other fixation feature to reduce or eliminate the likelihood that the piercing member 312 disengages from the nodule 208. Upon deployment of the second electrode 105, the first electrode 103 can continue to advance in the distal direction F. Further advancement of the first electrode 103 can increase the angle A2 between the centerline of the first electrode 103. In some embodiments, first electrode 103 can continue to advance in direction F such that the second electrode 105 is positioned proximal to the first electrode 103. In some embodiments, an insulating layer 113 on the first electrode 103 can help to reduce or eliminate the likelihood of damage to the airway wall 3 from electric current introduced to the first electrode 103.

Piercing through the airway wall or lumen in some of the embodiments described above may present some advantages in the treatment of lung tissue and nodules. Such transluminal approaches permit the energy delivery to be approximately centered into the mass to be treated, compared to intraluminal approaches that may remain the airway. At the same time, transluminal approaches are less invasive and may be able to access deeper sections of the lung with less trauma and complications than conventional transthoracic approaches.

In some embodiments, all or a portion of the one or more of the electrodes 103, 105 may be detachable and/or interchangeable with other electrodes. For example, the piercing tip 310 or the piercing end 312 may be configured to detach from the remainder of the respective electrode to which it is attached to. In some embodiments, the catheter system 100 can be sold with multiple piercing, tips 310, piercing ends 312, first electrodes 103, and/or second electrodes 105 (hereinafter referred collectively as detachable components). Each of the detachable components can be sized and shaped to treat a particular range of nodule sizes (e.g., width/volume) and/or to accommodate particular ranges of power requirements or fluid uses for the treatment of a particular nodule or other area of interest. In some embodiments, the appropriate detachable components can be chosen after visualizing the area of interest (e.g., nodule, tumor, and/or lesion) and/or after biopsying tissue from the area of interest. When detached while embedded in tissue, the detached section may be used as a fiducial marker or other indicator suitable to indicate the location of the area that was treated. This may be useful not only in post-treatment diagnoses, but also in serving as a navigational aid for subsequent treatment.

Because the lungs generally have airway sizes of decreasing diameter and increased convolution, treatment modalities may need to be varied in response to the pulmonary area being treated. The central lung, extending from the trachea to the larger (i.e., left and right) main bronchi, and the mid-lung region, which may comprise lobar and segmental bronchi, are typically large enough to be navigated with a bronchoscope. Accordingly, treatment of affected areas in the lung, which may include lung nodules and other such diseased regions, may be performed with relative ease in the central lung. Treatment into mid-lung region, while more difficult, can be performed using bronchoscope-based treatment methods. In particular, bronchoscopes with side-facing ultrasound probes (such as the Olympus EBUS® scope)

may be particularly well suited for treatment of regions of lung tissue such as lung nodules, especially those located on an opposite side of an airway wall that a bronchoscope is located on. Access to highly angulated lung regions may still be difficult in some situations.

Peripheral regions of the lung, however, comprise subsegmental bronchi leading to terminal bronchi and alveoli, and may be too small or too highly angulated to be navigated with traditional visualization means. Navigating to and treating such peripheral regions may thus require a bronchoscope or other guide means to be inserted as far as possible, followed by extension of a much smaller guide sheath into the peripheral regions. Guidance to the peripheral region in such cases may be provided using fluoroscopy or other non-bronchoscopic visualization methods. These methods may also be useful in larger airways that are highly angulated and thus difficult or impossible to reach via bronchoscopic approaches.

Bronchoscopes or other endoscopes provided with ultrasound probes or otherwise used in conjunction with ultrasound may also be used in conjunction with Doppler or other blood flow visualization means. Especially in a highly-vascularized environment such as the lung, visualization of blood flow may be advantageous to avoid causing excessive bleeding or delivering large amounts of energy to blood vessels.

Figure 4:
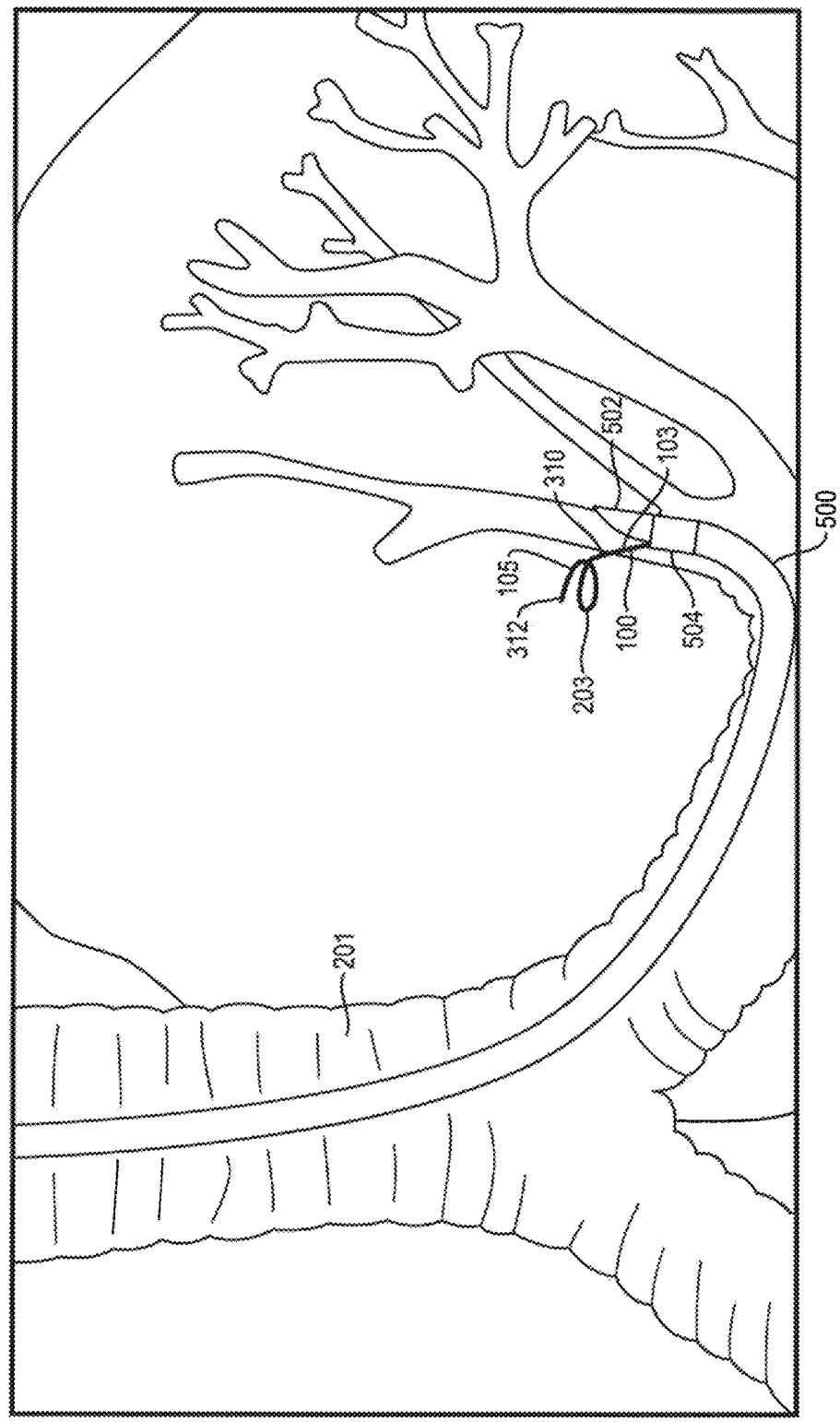
FIG. 4 is a view of the catheter of FIG. 1 deployed through an airway in conjunction with a bronchoscope containing an ultrasound probe.

FIG. 4 illustrates an embodiment of the catheter system 100 disposed within a bronchoscope 500 provided with a side-facing ultrasound probe 502 placed within an airway 201. An example of such a bronchoscope 500 is the EBUS® scope manufactured by Olympus. Preferably, the bronchoscope 500 is provided with at least one lateral port 504 extending from the bronchoscope working channel; this permits the catheter shaft 101 to extend through the port 504.

In some configurations, the first electrode 103, being preferably provided with a piercing tip 310, is bendable and flexible. In some configurations, the first electrode 103 and/or the piercing tip 310 may be bendable at an angle of at least 10°, preferably about 20°, about 30°, about 45°, about 55°, about 65°, about 75°, and even more preferably at least about 90°, relative to the longitudinal axis of the axial length of the airway. As such, when a region of lung tissue to be treated is located—for example, by use of the side-facing ultrasound probe 502—the first electrode 103 can be extended at least partially into that region of lung tissue by piercing through the airway 201. The first electrode 103 and/or piercing tip 310 may not necessarily need to be bendable, and can be used, for example, to pierce a tissue site disposed directly in front of the catheter system 100. In some configurations, the second electrode 105 and/or its piercing end 312 can be configured to extend from within the electrode 103 into the lung tissue distal of the airway wall. Some examples of flexible needles that may be used in conjunction with embodiments disclosed herein may be found in U.S. Application Ser. No. 61/604,457, filed Feb. 28, 2012, titled "LUNG BIOPSY NEEDLE," and U.S. application Ser. No. 13/777,854, filed on Feb. 26, 2013, titled "LUNG BIOPSY NEEDLE," both of which are hereby incorporated by reference herein in their entirety.

In some cases, however, and as discussed above, regions of lung tissue to be treated may be found in peripheral lung regions. In peripheral lung regions, the air passages are too small to be navigated with conventional bronchoscopes, and much smaller instrumentation must be used to navigate treatment methods and devices to regions of tissue within this region. Typically, a small diameter bronchoscope is navigated as deeply as possible in the lung, at which point a guide sheath may be extended to reach the peripheral tissue to be treated. Embodiments of the catheter system 100 may thus be miniaturized to fit into small bronchoscopes, for example those with a working channel having a 3 mm outer dimension and a 2 mm working channel. Guide sheaths may have an outer diameter of about 1.95 mm and a somewhat smaller inner channel, and the catheter system 100 and the sheath 101 may be configured to pass within these channels. Although some embodiments may not be able to reach into the smallest individual alveoli, these may be able to reach deeply enough into the lung so as to be positioned in an airway proximate a region to be treated.

In some configurations of the catheter system 100 configured to be guided to positions within the peripheral lung regions 203, the catheter system 100 (which may still be disposed within a guide sheath) may be guided using external guidance methods. For example, guidance may be effectuated via real time computerized tomography ("CT"), via electromagnetic navigation (e.g., the SuperDimension iLogic system), via various transthoracic tools, or via fluoroscopy.

Figure 5:
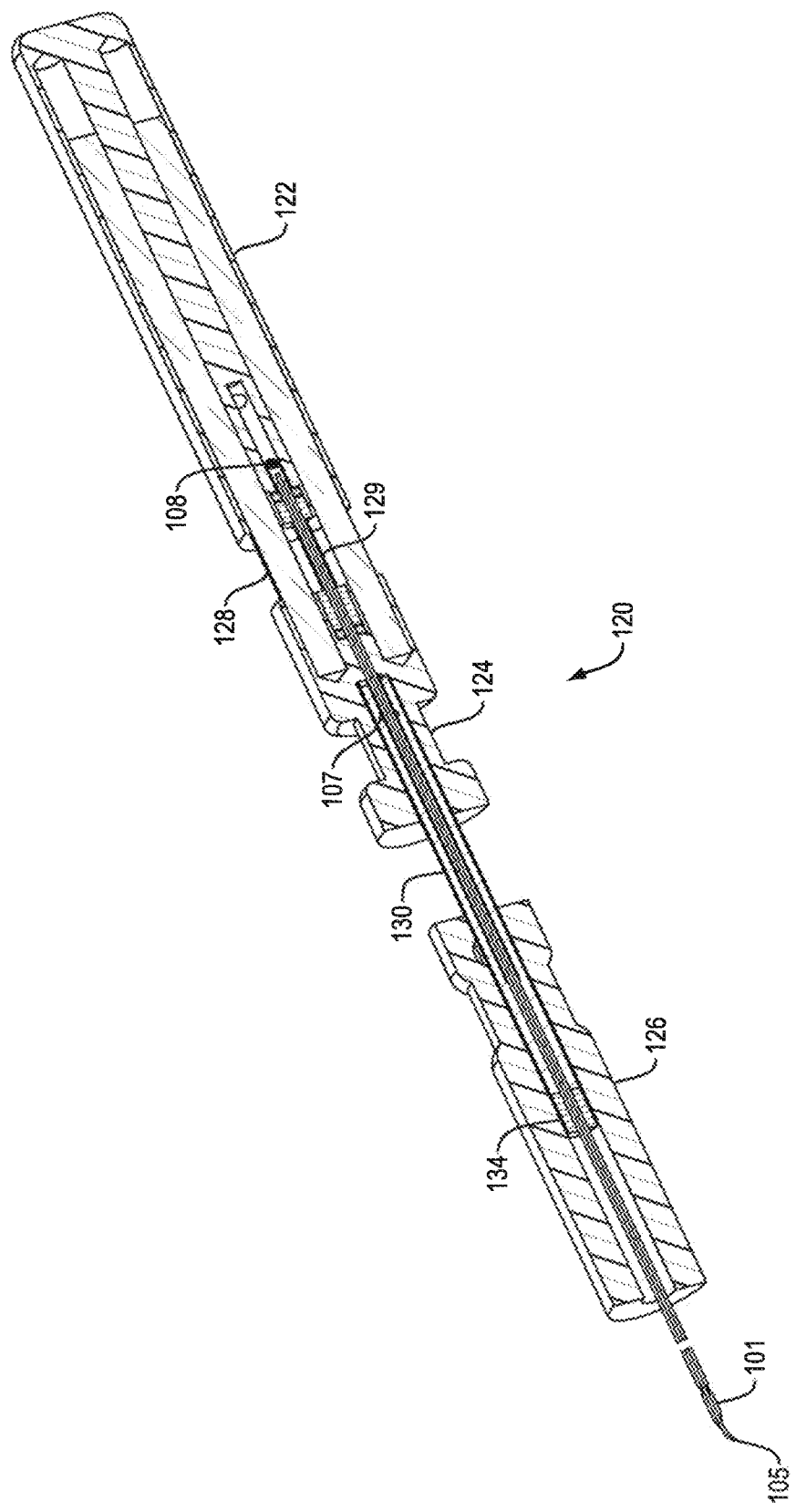
FIG. 5 is a detail of a handle portion of the catheter of FIG. 1.

FIG. 5 illustrates a cutaway view of an embodiment of the handle 120. Here, the handle 120 comprises a second activation toggle 122 that is preferably configured to extend the second electrode 105, wherein the proximal end of the second electrode 105 is attached within the second activation toggle 122 (for example, within a cavity). The second activation toggle 122 may be connected in a movable manner via one or more movable rods 128 to the first toggle 124. The first toggle 124 may be configured to extend the first electrode 103. Details of these steps will be described in FIGS. 6A-C.

In some configurations, a first hypotube 129 extends through a central passage of the first activation toggle 124 and into a handle base 126 and the second activation toggle 122. The first hypotube 129 can be fixedly attached within the first activation toggle 124, but remains in a movable (e.g., slidable) relationship with the handle base 126 and the second activation toggle 122. The first hypotube 129 also extends within a second hypotube 130 that is disposed in a movable manner (e.g., in a sliding manner) between the handle base 126 and the first activation toggle 124. The second hypotube 130 can be fixedly attached within the handle base 126, and can slide in relation to the first activation toggle 124.

The electrical lead 108 can be configured to be electrically connected through an aperture in the second activation toggle 122 to the second electrode 105. In some embodiments, a proximal portion of the second electrode 105 may extend along the entire length of the first hypotube 129 and be fixedly secured within a cavity in the second activation toggle 122. The electrical lead 108 may be connected to the second electrode 185 via a cable or other electrical connector, and may in some embodiments extend, when provided with suitable insulation, along all or part of the first hypotube 129. Preferably, the second electrode 105 and/or electrical lead 108 are insulated along their entire length, and particularly in relation to the catheter shaft 101.

In some configurations, the proximal end 110 of the catheter shaft 101 extends through the handle base 126 and the first activation toggle 124, and is received in a movable manner within the second activation toggle 122. The proximal end 110 can be fixedly attached within the handle base 126, for example via a bushing 134 (which may be placed entirely or partly within the second hypotube 130).

In some embodiments, the handle 120, and in some configurations the second activation toggle 122 of the handle 120, comprises one or more stops configured to reduce or eliminate the likelihood of various components, such as the first and second activation toggles 122, 124, from being overextended or detached. For example, the first hypotube 129 may comprise a stop with a nub or other projection that is configured to reduce or eliminate the likelihood of the hypotube being overextended. Such stops may also or alternatively be placed on the movable rods 128.

The first activation toggle 124 can have the electrical lead 107 connectable thereto. The electrical lead 107 can be configured to be electrically connected to the catheter shaft 101, for example through a conductive hypotube 129, both of which can be electrically conductive so as to transmit electricity to the first electrode 103. In other embodiments, the electrical lead 107 is configured to be electrically connected via the aperture to the first electrode 103 via a separate cable or wire.

Figure 6A:
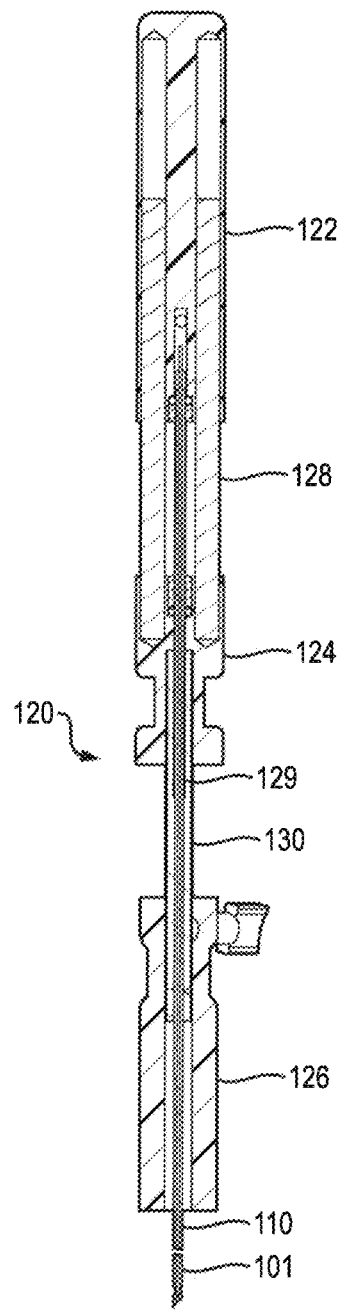
FIGS. 6A-6C illustrate deployment steps of the catheter of FIG. 1.
Figure 6B:
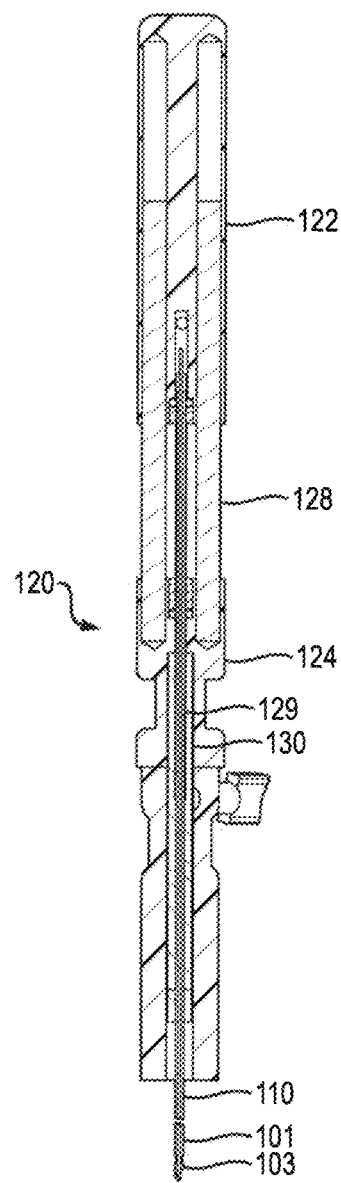
Figure 6C:
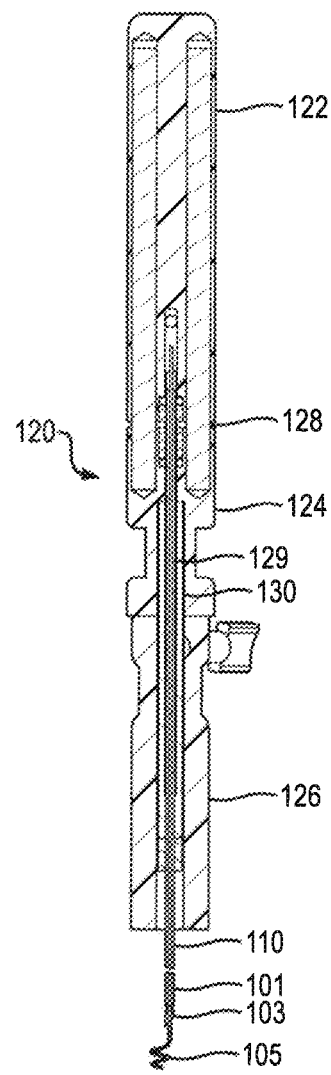

FIGS. 6A-C illustrate different deployment stages of the system 100. In general, embodiments of the catheter system 100 may be configured with a handle portion 120 that permits the electrodes to be engaged or disengaged (for example, extended or retracted) with relative ease by an operator. An example of such a system is illustrated here. For example, the handle 120 may be configured to have one or more activation toggles (e.g., as described above in FIG. 5) that permit the first electrode 103 to be extended from the catheter shaft 101 and/or the end of a bronchoscope or other such instrument that the catheter system 100 may be inserted into. FIG. 6A, illustrates the handle 120 in a state where the first electrode 103 is retracted within a working channel of a bronchoscope or guide sheath (not illustrated).

Turning now to FIG. 6B, the first activation toggle 124 has been moved distally toward the handle base 126. Preferably, the first activation toggle 124 is slid along the second hypotube 130, but other movement modes are envisioned, such as having a screwable or rotational engagement. This movement of the first activation toggle 124 may push the first electrode 103 out of the catheter shaft 101. In some configurations, the electrode 103 can be integral with the catheter shaft 101 and movement of the first activation toggle 124 may serve to advance the catheter shaft 101 and the first electrode 103 by a small distance, for example a distance sufficient to permit the electrode 103 to extend out of a bronchoscope working channel and/or guide sheath. In any event, when provided with a piercing tip 310, these arrangements may enable the first electrode 103 to pierce into and be placed into a tissue site. This may include, for example, piercing through an airway wall.

In FIG. 6C, with the first activation toggle 124 displaced, the second activation toggle 122 may then be moved distally in the direction of the first activation toggle 124. Preferably, the second activation toggle 122 is slid along the one or more slider rods 128 and/or the first hypotube 129. As mentioned above, alternate movement mechanisms are envisioned, including screwable or rotational engagements. The movement of the second activation toggle 122 permits the movement of the second electrode 105, thereby allowing the second electrode 105 to slide and extend from the first electrode 103. Preferably, this longitudinal movement embeds or fixes the second electrode 105 into the tissue to be treated. It will be noted that in some embodiments, all or part of the foregoing toggle mechanisms that permit engagement of the one or more electrodes may be motorized.

Figure 7:
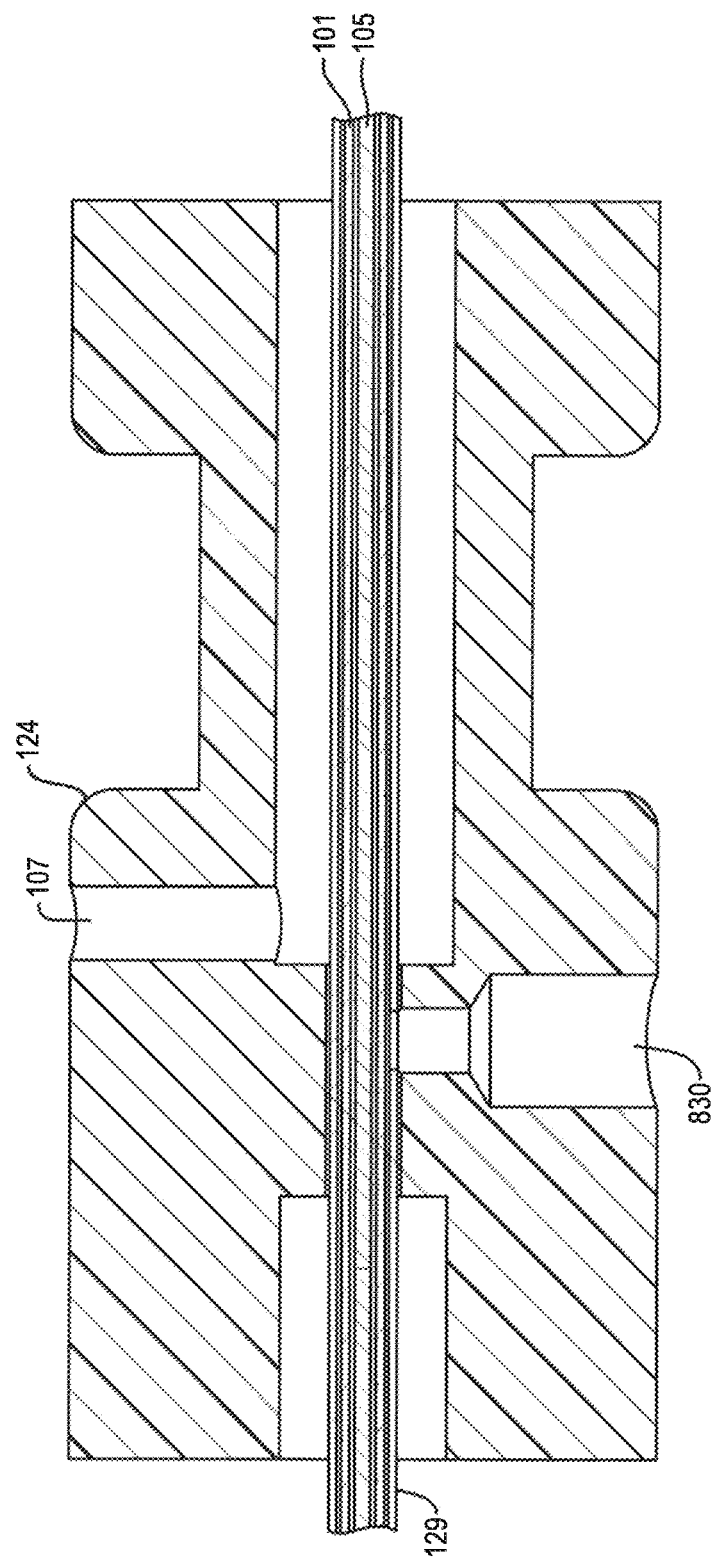
FIG. 7 is a detail of a fluid infusion port that may be present in the catheter of FIG. 1.

FIG. 7 illustrates a cutaway view of the first activation toggle 124. In some configurations, it may be desired to include a fluid port 830 in fluid communication with one or more of the electrodes 103, 105 and/or the tissue region to be treated. In some configurations, the fluid port 830 can be in fluid communication with the catheter shaft 101, and can thereby be connected to a source of fluid (described in greater detail below). For example, an aperture may be made into the first hypotube 129 such that fluid introduced through the fluid port 830 enters into the hypotube 129 and flows proximally toward the central cavity in the second activation toggle 122. The fluid may then flow down the hollow catheter shaft 101. In some configurations, appropriate seals and insulation can be provided to improve the mechanical and electrical integrity of the device.

In some configurations, the fluid port 830 may be disposed in the second activation toggle 122, or elsewhere on the device. In some configurations, the fluid port may communicate to a dedicated fluid channel that runs along or through the catheter shaft and/or electrodes. The location of the fluid port 830 may not necessarily be on the first activation toggle 124, and may instead be mounted on any other portion of the handle 120, or provided separately onto the catheter shaft 101.

Figure 8A:
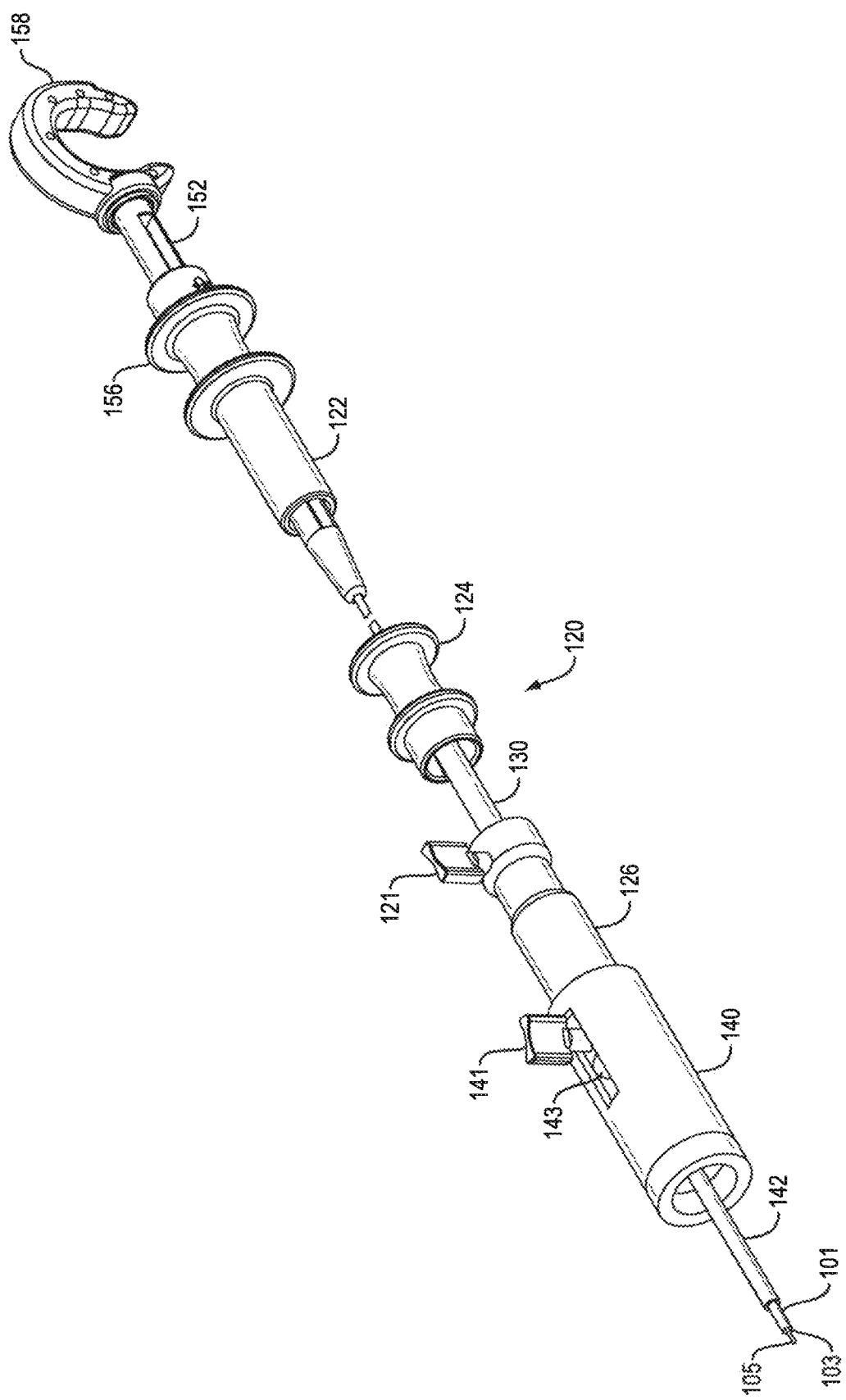

FIGS. 8A-D illustrate a variation of the embodiment described above in relation to FIGS. 6 and 7A-C. With reference now to FIG. 8A, an embodiment of a handle 120 that may be used with the system 100 comprises a handle base 126 that is connected in a movable manner to a first activation toggle 124 via a second hypotube 138. At the proximal end of the handle 120, a second activation toggle 122 is attached via a first hypotube 129 and/or catheter shaft 101. Although there are some similarities in the general functionality of this embodiment in comparison to the embodiment discussed previously, there are several changes and additional parts.

The handle 120 may comprise a bronchoscope attachment 140, optionally provided with a bronchoscope guide 142 attached at its distal end and extending in a distal direction. This attachment 140 is preferably configured to be secured to the exterior of the working channel of a bronchoscope, with the bronchoscope guide 142 being preferably extending at least partly into the working channel. Such an arrangement, while optional, may aid the operator in controlling and handling the catheter system 101.

Although some embodiments may provide for the bronchoscope attachment 140 to be integrated into or permanently attached to the handle base 126, the embodiment described provides for a removable bronchoscope attachment 140. Such an arrangement may permit different bronchoscope attachments to be supplied for use with different bronchoscope or endoscope types. In a preferred embodiment, the bronchoscope attachment 140 is secured to the handle base 126 by using a second thumb grip 141 attached to the handle base 126. The second thumb grip 141 can be received into a slot 143 and turned so as to tighten the second thumb grip 141 against the bronchoscope attachment 140, in some configurations after the attachment 140 and guide 142 have been set to the correct depth within the bronchoscope working channel. Other attachment mechanisms are contemplated, including various latches, screwing engagements, and the like.

As with the embodiment previously described, the thumb grip 121 may be provided to aid an operator in manipulating and controlling the catheter system 101. In some embodiments, the thumb grip 121 may also be used to lock the piercing end 310 of the first electrode 103 after it has been inserted into tissue, using deployment steps such as those described below, for example but without limitation. In some configurations, the second activation toggle 122 can be configured to be connected to the remainder of the handle 120 via the first hypotube 129 and/or the catheter shaft 101. These respective parts being generally flexible, the second activation toggle 122 can be deployed from any angle. A further advantage is that in some embodiments, as illustrated, the toggle 122 may be more ergonomic and easily grasped compared to other embodiments.

Figure 8B:
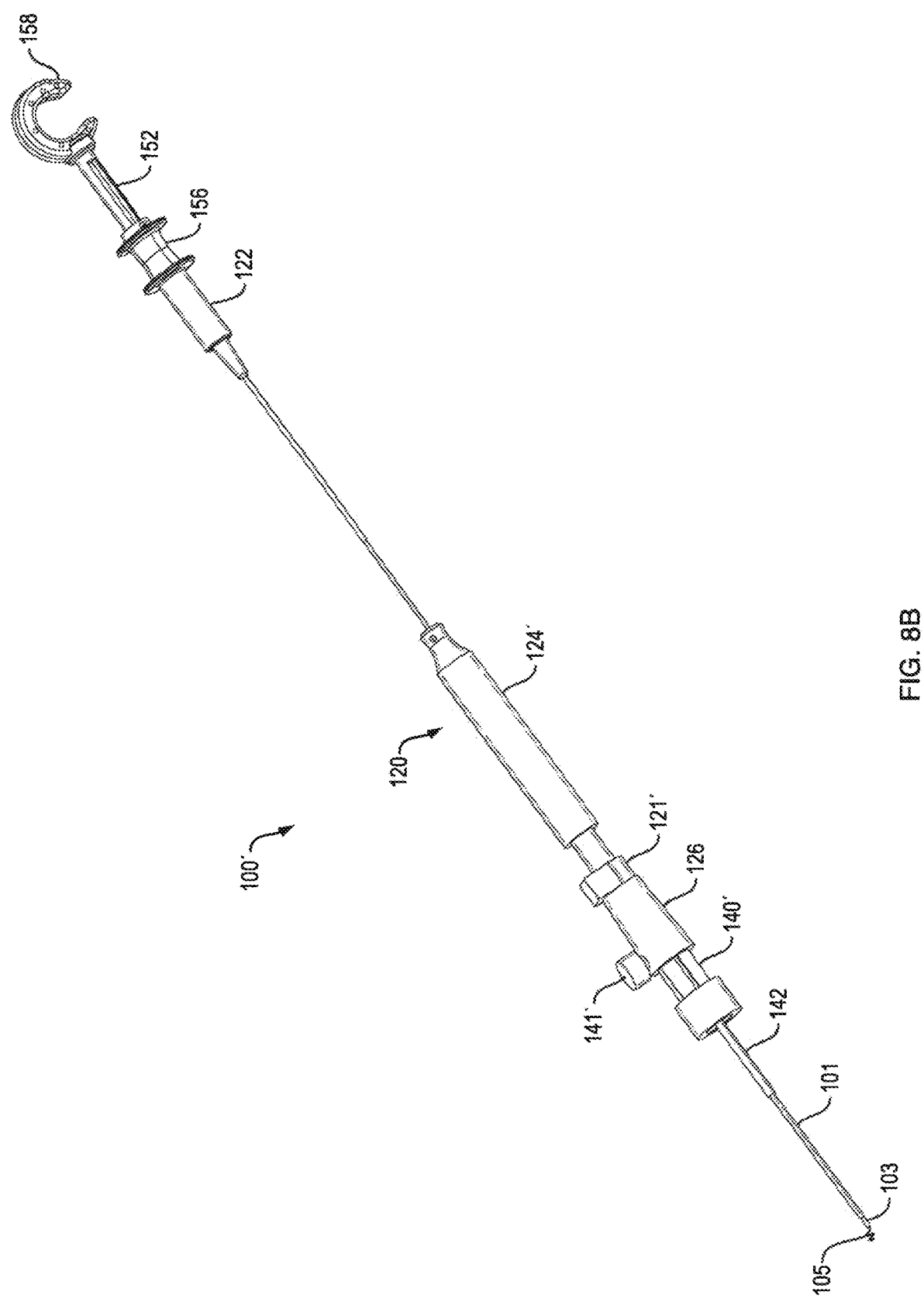
Figure 8D:
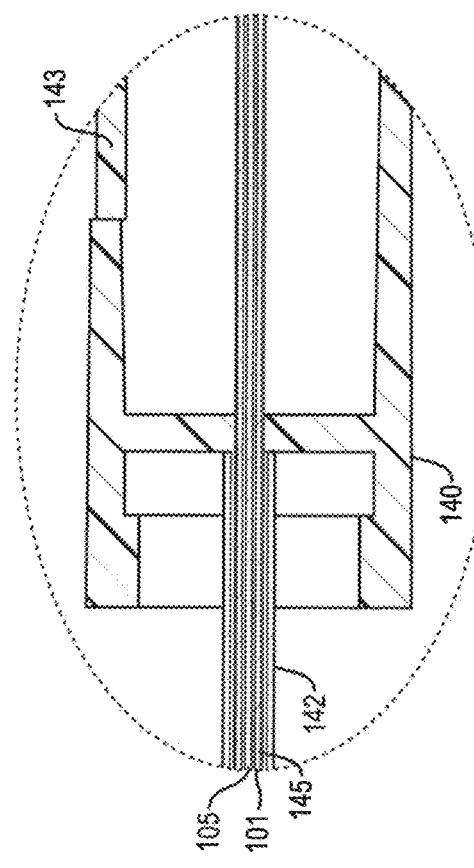

FIGS. 8B-D illustrate cutaway views of the embodiment discussed above in relation to FIG. 8A. In this embodiment, the second activation toggle 122 comprises a static grip 152, which preferably comprises a central cavity into which the proximal end of the second electrode 105 may be received. The proximal end of the second electrode 105 can be attached to a holder 154. The holder 154 may then be secured or attached to the static grip 152. In some embodiments, an ergonomic knob 158 may be provided at a distal end of the static grip 152. The ergonomic knob 158 may be C-shaped, or otherwise adapted to be grasped by a thumb or finger of an operator.

A movable grip 156 can be disposed around the static grip 152, and can be movable in relation to it. In some configurations, the movable grip 156 can be movable in a longitudinal axial direction with respect to the static grip 152. As such, moving the movable grip 156 in a proximal direction (i.e., toward the ergonomic knob 158) will act to move the electrode 105 in a distal direction, thereby deploying it from the distal end of the catheter shaft 101. In some embodiments, the catheter shaft 101 and/or first hypotube 129 may be attached or in a frictional engagement with the movable grip 156, so as to permit the second electrode 105 to be longitudinally axially displaced in relation to these.

In some configurations, an opposite engagement can be used in which the holder 154 is attached to the movable grip 156, such that moving the movable grip 156 in a distal direction (i.e., away from the ergonomic knob 158) will deploy the second electrode 105. In this embodiment, the catheter shaft 101 and/or first hypotube 129 may remain attached or in frictional engagement with the static grip 152. Other engagements are also possible. In some embodiments, the second activation toggle 122 (or any other part of the handle 120) may also be provided with a lock or other means to prevent accidental deployment the catheter system 101. Additionally, it will be recognized that electrical leads 107 and 108, may be disposed on the first and second activation toggles 124, 122, or elsewhere on the handle 120. In some configurations, the first electrical lead 107 (connected or connectable to the first electrode 103) is attached to the first activation toggle 124. In some configurations, the second electrical lead 108 (connected or connectable to the second electrode 105) is attached to the second activation toggle 122, for example on the movable grip 156 via a bolt or other solid attachment. Further, a fluid entry port 830 may also be present on the first activation toggle 124 or elsewhere on the handle 120 in a manner similar to what has been previously described. For example, the fluid entry port 830 can be located on the first activation toggle 122.

With reference now to the distal end of the handle 120 illustrated in FIG. 8C, the relationship between various components comprising the illustrated catheter system 100 can be clarified. As illustrated, the bronchoscope guide 142 can be attached to the bronchoscope attachment 140. The guide 142 can be constructed from a lubricious and flexible material, including polymers, such as polyurethane, polytetrafluoroethylene, high density polyethylene, PEEK, polyamide, and the like. The bronchoscope guide 142 (together with the bronchoscope attachment 140) may be helpful in allowing an operator to position the catheter shaft 101 and other components of the system 100 into a bronchoscope working channel.

A guide sheath 145 is optionally disposed on an outer surface of the catheter shaft 101, and can extend distally past the distal end of the bronchoscope guide 142 and proximally into the handle base 126. It may be secured therein, for example by using the second thumb grip 141. The guide sheath 145 can be constructed from a flexible and lubricious material (including polymers such as polyurethane and polytetrafluoroethylene), and can be preferably at least partly abrasion resistant. As such, the guide sheath 145 can be used to protect the distal end 109 of the catheter shaft 101, such as the piercing ends 310, 312. Further, the guide sheath 145 can be sized to extend at least the entire length of the bronchoscope working channel. Consequently, the guide sheath 145 can also be used to protect the bronchoscope working channel from abrasions or other damage resulting from the catheter shaft 101. The catheter shaft 101 can have the second electrode 105 disposed there within.

In some embodiments, the guide sheath 145 may be extended far past the bronchoscope working channel so as to reach deep lung regions or lung regions that are too narrow or angled to be reachable by a traditional bronchoscope. In such cases, the guide sheath 145 may be guided fluoroscopically or using other navigational methods to a region of tissue to be treated. Consequently, some embodiments may be provided with a localization marker such as a radioopaque marker disposed at the end of the guide sheath so as to aid in navigation.

Turning now to FIG. 8D, an enlargement of an embodiment of the second activation toggle 122 is illustrated. The catheter shaft 101 can extend all the way to the second activation toggle 122, and may be attached or in frictional engagement with the static grip 152 or the movable grip 156. In some configurations, the second electrode 105 is disposed within the catheter shaft 101 and extends into and is attached to the holder 154. In some configurations, the first hypotube 129 may be provided. Instead of being disposed on the outside of the catheter shaft as in the configuration illustrated in FIG. 5, the first hypotube 129 can be disposed on the interior of the catheter shaft 101, and over the proximal end of the second electrode 105. As such, the hypotube 129 may be useful to provide additional rigidity and structural support to the second electrode 105. Further, the hypotube 129 may be useful in maintaining fluid introduced via a fluid port 830 within the catheter shaft 101.

Figure 8E:
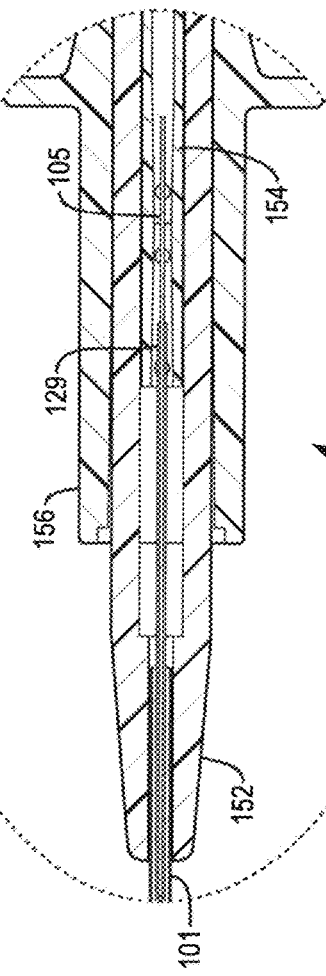
FIG. 8E illustrates another embodiment of a handle portion of a catheter that is arranged and configured in accordance with certain features, aspects and advantages of the present disclosure.

FIG. 8E illustrates another embodiment of a catheter system 100'. Numerical reference to components the same as previously described, except that a prime symbol (') has been added to the reference. Where such references occur, it is to be understood that the components are the same or substantially similar to previously-described components. For example, the catheter system 100' includes a first activation toggle 124' that has an elongated body. The catheter system 100' can include handle 120'. The handle 120' can include a thumb pad 121' shaped generally as a collar with a protrusion extending from the handle 120'. In some embodiments, the catheter system 100' includes a bronchoscope attachment 140' configured to slidable engage an interior of a handle base 126.

Figure 9:
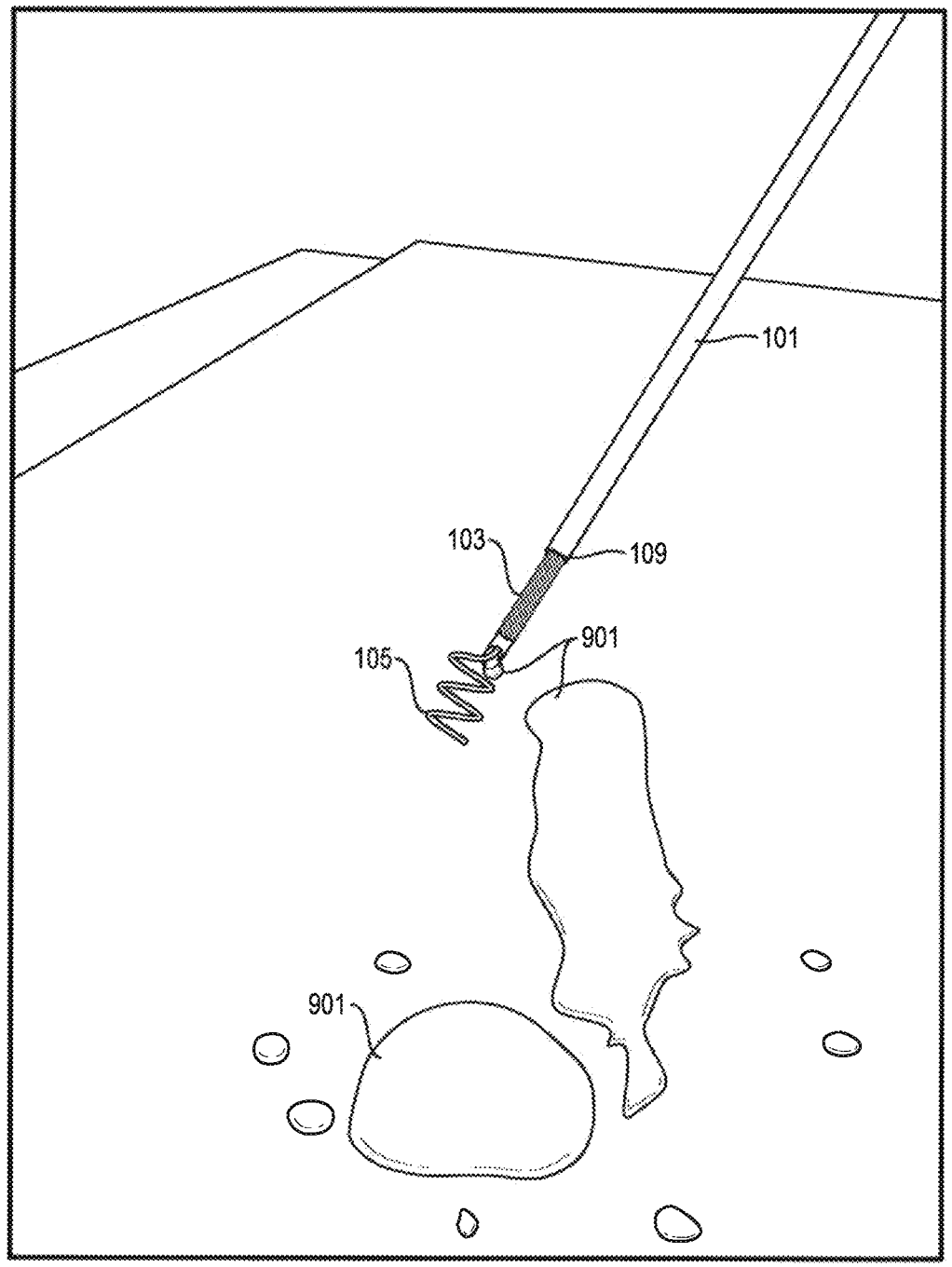
FIG. 9 is a close-up of the distal tip of a catheter, illustrating a saline solution being dispensed therefrom.

FIG. 9 illustrates the distal end 109 of the catheter shaft 101. As illustrated, a fluid source has been connected to the catheter shaft 101 (for example via the fluid port 830), and fluid 901 is shown exiting the space between the first electrode 103 and the second electrode 105. In this manner, fluid 901 can be injected proximate the respective electrodes 103, 105 when the electrodes are deployed in a region of tissue to be treated. Of course, other configurations are possible, and in some configurations the fluid source does not leave the catheter shaft 101, and may be sealed within all or part of the system 101, for example in a recirculating arrangement. In some configurations, the fluid 901 may circulate within one or both of the first and second electrodes 103, 105. Also, other configurations may permit the fluid 901 to be dispensed or injected from other regions, including apertures proximal to the electrodes 103, 105 along the catheter shaft 101, for example. In some configurations, one or both of the first and second electrodes 103, 105 may be hollow and at least partially porous (i.e., using a sintered manufacturing method) or provided with one or more small holes, thereby permitting the fluid 901 to be dispensed therefrom.

The fluid 901 may be used for several purposes. In one embodiment, the fluid 901 acts to cool the electrodes 103, 105. In general, when electrodes are heated, for example when delivering RF energy, electrode efficiency may be reduced due to increased impedance. As a result, cooling the electrodes may be beneficial to maintaining electrode performance during energy application to tissue. While the fluid 901 may be a liquid, in some embodiments it may be a gel or other flowable substance.

The fluid 901 may also be beneficial in reducing or eliminating the likelihood of tissue charring when delivering energy to heat the tissue. In particular, for RF ablation and other electrically-based heating techniques, if tissue is heated at too high of a temperature, the tissue is likely burn or char. Once this occurs, the impedance of the tissue increases, thereby reducing or eliminating the likelihood of the ablation treatment reaching a larger area of tissue due to the greatly reduced tissue conductivity. Therefore, a larger tissue region can be treated with heat as long as the tissue is maintained at a temperature below which the tissue burns or chars. The fluid 901 may be useful for promoting this result.

Additionally, in embodiments where the fluid 901 is injected into tissue surrounding the electrodes 103, 105, the fluid 901 may be beneficial in conducting heat to a larger area of tissue. This may enable a larger area of tissue to be treated than if no fluid were injected. In RF ablation in particular, care must be taken to not significantly overheat or "char" the tissue surrounding the electrodes while heating the tissue sufficiently to denature, deactivate, or kill the targeted tissue. By injecting fluid 901 in the vicinity of the tissue surrounding the electrodes, heat may therefore be spread to a wider area.

In some embodiments, the fluid 901 comprises a saline solution. In some embodiments, the solution may comprise between about 0.1% to about 34% saline, more preferably about 0.7 to about 1% saline, and even more preferably about 0.9% saline. Other solutions containing electrolytes are possible, including phosphate buffer saline (PBS) and the like. The fluid 901 may in some embodiments also comprise a conductive gel. When using a saline or otherwise electrolytic solution in a fluid 901 that is injected into the tissue surrounding the electrodes, tissue conductivity may be increased. As described above, this may increase the dimensions of the area treatable with the electrodes. In particular, for methods that heat tissue with electrical energy (e.g., RF ablation), such heating may dry tissue, thereby reducing, its conductivity. The addition of an electrolytic solution may thereby also help mitigate any such effect. In some embodiments, it has been found that a saline infusion rate preferably between about 1 and about 10 ml/min, more preferably about 2-6 ml/min, functions well as a balance between increasing the treated area while reducing or eliminating the likelihood of injecting of large volumes of fluid into the tissue (which may open up a void space or fluid pocket which may be undesirable in some treatment modalities).

Because lung tissue is less dense than tissue in other body organs and regions (e.g., the liver), such lung tissue may have a higher impedance that can hamper efforts to deliver energy sufficient to treat or ablate tissue. As such, dispensing a saline solution may be more advantageous in pulmonary tissue compared to other, denser types of tissue. Particularly, but not exclusively, when coupled with embodiments using transluminal piercing electrodes that extend through an airway wall (rather than being disposed in contact with the airway wall), this may permit treatment of lower-density tissue surrounding, a higher-density mass such as a lung nodule. This may also be advantageous in the treatment of lower-density nodules, such as ground-glass opacity nodules.

In any event, the ability to treat tissue with higher impedance may be especially useful when treating lung nodule margins. Whereas conventional ablation or energy delivery treatment piques may not be able to account for differences in tissue impedance between higher density nodules and lower density tissue surrounding the nodules, it is believed that use of at least saline or electrolytic fluid may be advantageous in treating margins around tissue by reducing the impedance of the lower density tissue. For example, a lung nodule with an approximate diameter of less than 3 cm may have margins removed around it that are at least 2 cm in size. Accordingly, treatment of the lower-density tissue margins surrounding a higher density nodule may be performed in a single step through the infusion of fluid.

In some embodiments, the fluid 901 may comprise additional agents. For example, medicants, such as antimicrobial, antiviral, anticancer, anti-tumor, anti-inflammatory, pro-inflammatory, and other such compounds or substances may be introduced. Cells, including stem cells, as well as cell growth promoters or inhibitors may also be used. The fluid 901 or a component thereof may also coagulate, solidify, or act as a sclerosing agent, for example after being heated, cooled, or activated (e.g., via a polymerization initiator). Such a fluid may be useful if a void is created as a result of fluid delivery, or so as to encapsulate the tissue region being treated. Examples of such fluids 901 comprise heat curing epoxies, thermoset resins (e.g., polyurethane, polyester), and protein complexes (e.g., egg whites).

Further, the fluid 901 may also comprise visualization agents. These agents may be beneficial in indicating the extent to which the fluid 901 has spread within the tissue being treated, and could be used to demarcate an approximate treatment area. In some embodiments, the visualization agents may comprise pigmented or colored substances. The visualization agents may also be at least partially radioopaque, or act as MRI-contrast enhancing agents. In some embodiments, the visualization agent may include antibodies or other indicators capable of binding to a particular tissue type (e.g., cellular cancer markers) so as to permit visualization of an affected region of tissue.

The catheter system 101 may also comprise additional sensors. These sensors are preferably configured to monitor one or more attributes of the system 101 and/or its effect on the tissue being treated. A non-limiting example of some monitored attributes that may be monitored include temperature monitoring (including for example monitoring of the treatment site, of the fluid, and/or of the electrodes), monitoring of electrical parameters associated with the electrodes (including for example impedance, voltage, and/ or current), and monitoring of the fluid flow rate and amount thereof dispensed. When monitoring temperature, some embodiments may be configured to have one or more temperature sensors able to detect the temperature of the surrounding tissue. This temperature sensor may be attached or integrated with one or more of the first and second electrodes 103, 105, or in some embodiments may be provided as a separate temperature probe.

In some embodiments, an impedance sensor may be useful to monitor the impedance of either or both of the electrodes and tissue being treated, and may be integrated into the electrodes or present as a separate sensor. Impedance may be a useful measurement to determine whether the electrodes are being overheated, whether the tissue being treated is dehydrated, and/or whether the tissue is being overheated, which may result in the tissue charring or burning. As previously noted, charred or burned tissue will have a markedly higher impedance, which consequently requires greater power to ablate, but also limits the extent to which energy can be dispersed into the surrounding tissue.

The catheter system 100 may be provided with a feedback mechanism configured to change one or more treatment attributes based upon monitored attributes received from one or more sensors, including the sensors described above, or time. The feedback mechanism may be used to change treatment attributes including the amount and type of power being applied to the tissue, the frequency of the power applied, the flow rate of the fluid, and other such attributes.

In one embodiment, the feedback mechanism may stop or decrease the application of power via the electrodes if the tissue or electrode temperature or impedance increases at too high of a rate or beyond a predetermined limit. Additionally, the feedback mechanism may be used to trigger one or more predefined treatment modes, although such predefined treatment modes may not necessarily need to be triggered by the feedback mechanism or any monitored attribute in particular, and may be used independently of such (for example, after passage of a certain time period rather than in response to one more monitored attributes or treatment attributes). A predefined treatment mode, may, for example, include time intervals where application of power is modulated or made intermittently active. A feedback mechanism may, for example, be used to modulate the power applied based on the temperature, and could lower the power applied during a predetermined time interval when the tissue reaches a certain temperature, and raise the power applied after that time interval if the tissue temperature has decreased. The time intervals and other predefined treatment modes may also be determined algorithmically based on real-time monitoring of the tissue and/or electrodes, and are not necessarily determined or defined prior to beginning of the treatment.

Figure 10A:
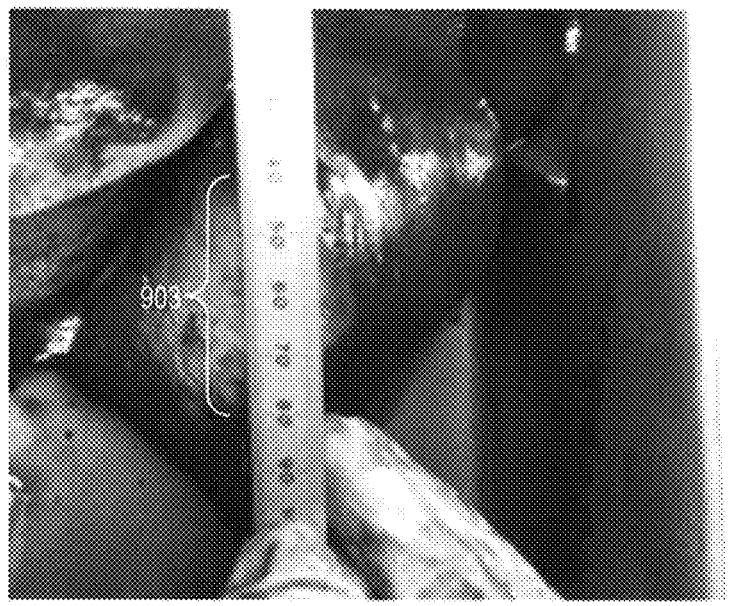
FIGS. 10A and 10B are photographs of an experiment illustrating differences in ablation zones obtained with and without saline infusion.
Figure 10B:

FIGS. 10A-B illustrates an experiment comparing the effects of saline infusion with RF ablation compared to RF ablation without saline infusion. FIG. 10A illustrates a sample of sectioned tissue where RF ablation in conjunction with a 0.9% saline solution was infused while energy delivery took place. The introduction of saline increases the total amount of energy required to ablate the tissue at the area of interest. The darker area 903 measures approximately 40 mm in diameter, with strong tissue discoloration showing the extent to which the treated tissue was heated. Without wishing to be bound by theory, it is believed that the saline infusion, as described above, increased the conductivity of the tissue, cooled the electrodes, and conducted heat into the tissues without causing significant tissue charring. This is in contrast with the tissue sample in FIG. 10B, where no saline ablation was used. Here, the darker area 903 measures approximately 25 mm in diameter. It will be noted that the darker tissue regions 903 do not necessarily denote the entire area treated by RF ablation, and the treated tissue area may extend beyond any darkened area without necessarily displaying discoloration.

Figure 11:
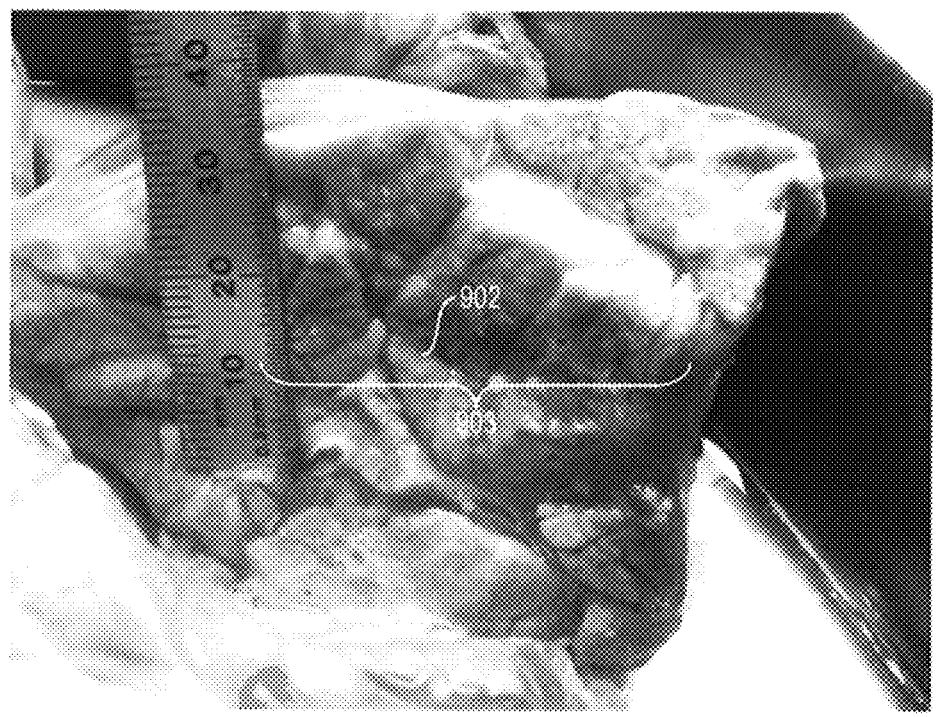
FIG. 11 is a photograph of illustrating an ablation zone obtained using an embodiment of a catheter described herein.

FIG. 11 is a photograph of an experiment where RF ablation was used through an airway wall to ablate nearby lung tissue. Here, an embodiment of the catheter system 101 (not illustrated) was navigated through a patient's lungs to an airway section 902 proximal to a lung nodule (not illustrated). After piercing the airway wall, RF ablation using 0.9% saline solution was applied. The bracket 903 illustrates the diameter of the visually ablated zone. In this embodiment, the diameter of the ablation zone 903 was approximately 35 mm.

Figure 12:
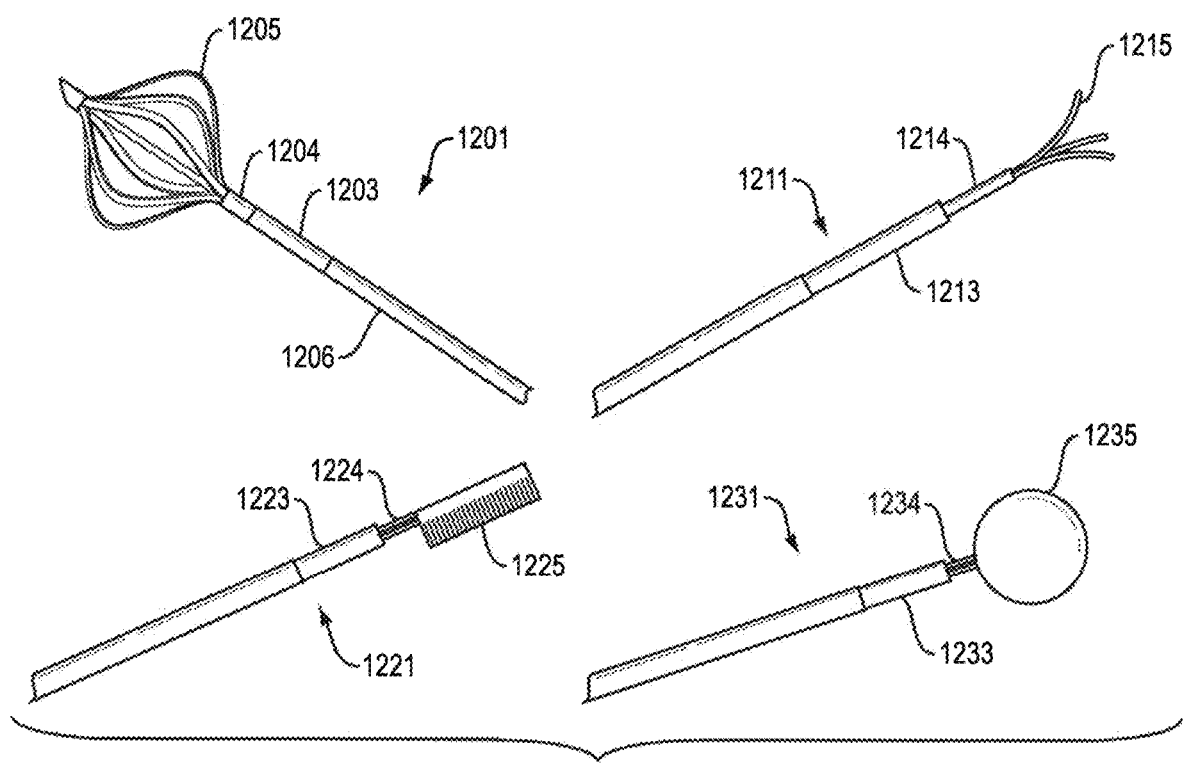
FIG. 12 illustrate embodiments of different electrode types that may be used in conjunction with the catheters described herein.

FIG. 12 illustrates additional electrode assembly configurations that may be used in some embodiments of the catheter system 100. Electrode assembly 1201 is an expanding "basket" type electrode with a first proximal electrode 1203 and a second distal electrode 1205, separated by an insulator portion 1204. An additional insulator portion 1206 may also be present proximal of the first electrode 1203. When deployed and pushed against or into tissue, the multiple strands that make up the "basket" of the second electrode 1205 push apart, thereby expanding the region that may be treated with electrical energy.

Electrode assembly 1211 illustrates an embodiment of a multi-wire penetrating electrode. Here, the first proximal electrode 1213 is separated from the multi-wire second electrode 1215 by an insulator portion 1214. When deployed or pushed against or into tissue, the individual wires of the second electrode 1215 penetrate into tissue, thereby increasing the zone that may be treated with electrical energy. Additionally, the individual wires of the second electrode 1215 may also serve to fixate the electrode 1215 into the tissue being treated.

Electrode assembly 1221 illustrates an embodiment of an electrode with a straight coil, similar to the electrode design illustrated in FIGS. 3A-B, but where a second distal electrode 1225 will not retract into a first electrode 1223. The electrodes are separated from each other by an insulating portion 1224.

Electrode assembly 1231 illustrates an embodiment of an electrode with a first electrode 1233 and a spherical coiled second electrode 1235. The respective electrodes are separated from each other by an insulating section 1234.

Of course, it will be clear that the above electrode types, as well as the other electrodes described herein, are non-limiting embodiments, and that other electrode types are possible. In terms of electrode design, in some embodiments it may be preferable to increase the total surface area of the electrode, in particular the second electrode or any electrode which extends into tissue. Electrodes comprising additional fingers or prongs may thus be desirable. Further, some embodiments may comprise one or more electrodes that are roughened or textured, or which may have nanoparticles embedded or sintered thereto, or other nanometer or micrometer size features deposited, etched, or machined thereupon. A notch or other channel may also be provided on some embodiments of electrodes described herein, and may be used to aid in delivering fluid 901 to the tissue being treated.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

What is claimed is:

1. A method of delivering energy to a region of lung tissue to be treated, the method comprising:
    inserting a catheter into a patient's airway, wherein a distal end of the catheter comprises a first electrode and a second electrode received in a sliding manner within the first electrode and configured to be extendable therefrom;
    navigating the catheter to an airway proximate the region of lung tissue to be treated;
    piercing the airway with the first electrode so as to position the first electrode into or near the region of lung tissue to be treated;
    extending the second electrode from a distal end of the first electrode into the region of lung tissue to be treated;
    activating a power source configured to deliver a therapeutic amount of energy to the region of lung tissue to be treated, wherein the power source is connected via a first electrical lead connected to the first electrode and a second electrical lead connected to the second electrode; and
    delivering energy to the region of lung tissue to be treated, wherein when a distal end of the second electrode extends distally from the first electrode, a portion of the second electrode that is extended from the first electrode changes from a first configuration to a second configuration,
    wherein the second configuration comprises a helical configuration.

2. The method of claim 1, further comprising inserting the catheter into a bronchoscope, the bronchoscope being inserted into the patient airway.

3. The method of claim 1, further comprising changing an amount of power delivered by the power source in response to a feedback mechanism responsive to at least one monitored attribute.

4. The method of claim 1, wherein the first configuration is not a helical configuration.

5. The method of claim 4, wherein in the first configuration the second electrode conforms to a channel within the first electrode.

* * * * *